United States Patent
Panescu

(10) Patent No.: US 11,534,227 B2
(45) Date of Patent: *Dec. 27, 2022

(54) HIGH-RESOLUTION MAPPING OF TISSUE WITH PACING

(71) Applicant: EPiX Therapeutics, Inc., Santa Clara, CA (US)

(72) Inventor: Dorin Panescu, San Jose, CA (US)

(73) Assignee: EPiX Therapeutics, Inc., Santa Clara, CA (US)

(*) Notice: Subject to any disclaimer, the term of this patent is extended or adjusted under 35 U.S.C. 154(b) by 1005 days.

This patent is subject to a terminal disclaimer.

(21) Appl. No.: 16/231,304

(22) Filed: Dec. 21, 2018

(65) Prior Publication Data

US 2019/0125427 A1    May 2, 2019

Related U.S. Application Data

(63) Continuation of application No. 15/179,861, filed on Jun. 10, 2016, now Pat. No. 10,166,062, which is a
(Continued)

(51) Int. Cl.
*A61B 18/12* (2006.01)
*A61B 18/14* (2006.01)
(Continued)

(52) U.S. Cl.
CPC .......... *A61B 18/1206* (2013.01); *A61B 5/283* (2021.01); *A61B 5/4836* (2013.01);
(Continued)

(58) Field of Classification Search
CPC .......... A61B 2018/00351; A61B 2018/00357; A61B 2018/00386; A61B 2018/00375;
(Continued)

(56) References Cited

U.S. PATENT DOCUMENTS 4,190,053 A    2/1980    Sterzer
4,197,860 A    4/1980    Sterzer
(Continued)

FOREIGN PATENT DOCUMENTS

EP    0746372    5/2003
EP    1008327    10/2008
(Continued)

OTHER PUBLICATIONS

China National Intellectual Property Administration, Notice on the Third Office Action, for corresponding Application No. 201580073126.4, dated May 26, 2020, 15 pages.
(Continued)

*Primary Examiner* — Eun Hwa Kim
(74) *Attorney, Agent, or Firm* — Michael Best & Friedrich LLP

(57) ABSTRACT

According to some embodiments, a method of confirming successful ablation of targeted cardiac tissue of a subject using a high-resolution mapping electrode comprises pacing said cardiac tissue at a predetermined pacing level to increase the heart rate of the subject from a baseline level to an elevated level, the predetermined pacing level being greater than a pre-ablation pacing threshold level but lower than a post-ablation pacing threshold level, delivering ablative energy to the ablation electrode, detecting the heart rate of the subject, wherein the heart rate detected by the high-resolution mapping electrode is at the elevated level before the post-ablation pacing threshold level is achieved, and wherein the heart rate detected by the high-resolution mapping electrode drops below the elevated level once ablation achieves its therapeutic goal or target, and terminating the delivery of ablative energy to the ablation electrode after the heart rate drops below the elevated level.

18 Claims, 8 Drawing Sheets

Related U.S. Application Data continuation of application No. PCT/US2015/061360, filed on Nov. 18, 2015.

(60) Provisional application No. 62/193,547, filed on Jul. 16, 2015, provisional application No. 62/081,710, filed on Nov. 19, 2014.

(51) Int. Cl.
*A61N 1/37* (2006.01)
*A61N 1/365* (2006.01)
*A61N 1/05* (2006.01)
*A61B 5/00* (2006.01)
*A61B 5/283* (2021.01)
A61B 18/00 (2006.01)
A61B 5/318 (2021.01)

(52) U.S. Cl.
CPC .......... *A61B 18/12* (2013.01); *A61B 18/1492* (2013.01); *A61N 1/0565* (2013.01); *A61N 1/36514* (2013.01); *A61N 1/371* (2013.01); *A61B 5/318* (2021.01); *A61B 18/14* (2013.01); *A61B 2018/00577* (2013.01); *A61B 2018/00666* (2013.01)

(58) Field of Classification Search
CPC .......... A61B 2018/00839; A61B 2018/00577; A61B 2018/00666; A61B 18/12; A61B 18/14; A61B 18/1492; A61N 1/371; A61N 1/36514; A61N 1/0565
See application file for complete search history.

(56) References Cited

U.S. PATENT DOCUMENTS

| | | |
|---|---|---|
| 4,346,716 A | 8/1982 | Carr |
| 4,557,272 A | 12/1985 | Carr |
| 4,614,514 A | 9/1986 | Carr et al. |
| 4,632,127 A | 12/1986 | Sterzer |
| 4,647,281 A | 3/1987 | Carr |
| 4,686,498 A | 8/1987 | Carr et al. |
| 4,715,727 A | 12/1987 | Carr |
| 4,727,874 A | 3/1988 | Bowers et al. |
| 4,774,961 A | 10/1988 | Carr |
| 4,815,479 A | 3/1989 | Carr |
| 4,922,912 A | 5/1990 | Watanabe |
| 4,945,912 A | 8/1990 | Langberg |
| 4,955,382 A | 9/1990 | Franz et al. |
| 4,979,510 A | 12/1990 | Franz et al. |
| 5,073,167 A | 12/1991 | Carr et al. |
| RE33,791 E | 1/1992 | Carr |
| 5,105,808 A | 4/1992 | Neuwirth et al. |
| 5,149,198 A | 9/1992 | Sterzer |
| 5,176,146 A | 1/1993 | Chive et al. |
| 5,198,776 A | 3/1993 | Carr |
| 5,230,349 A | 7/1993 | Langberg |
| 5,282,840 A | 2/1994 | Hudrlik |
| 5,334,141 A | 8/1994 | Carr et al. |
| 5,334,193 A | 8/1994 | Nardella |
| 5,344,435 A | 9/1994 | Turner et al. |
| 5,354,325 A | 10/1994 | Chive et al. |
| 5,364,336 A | 11/1994 | Carr |
| 5,370,676 A | 12/1994 | Sozanski et al. |
| 5,383,874 A | 1/1995 | Jackson et al. |
| 5,385,146 A | 1/1995 | Goldreyer et al. |
| 5,398,683 A | 3/1995 | Edwards et al. |
| 5,456,682 A | 10/1995 | Edwards et al. |
| 5,462,521 A | 10/1995 | Brucker et al. |
| 5,485,849 A | 1/1996 | Panescu et al. |
| 5,487,391 A | 1/1996 | Panescu |
| 5,494,042 A | 2/1996 | Panescu et al. |
| 5,514,130 A | 5/1996 | Baker |
| 5,522,815 A | 6/1996 | Durgin, Jr. et al. |
| 5,531,662 A | 7/1996 | Carr |
| 5,540,655 A | 7/1996 | Edwards et al. |
| 5,546,940 A | 8/1996 | Panescu et al. |
| 5,549,639 A | 8/1996 | Ross |
| 5,562,619 A | 10/1996 | Mirarchi et al. |
| 5,577,509 A | 11/1996 | Panescu et al. |
| 5,582,589 A | 12/1996 | Edwards et al. |
| 5,582,609 A | 12/1996 | Swanson et al. |
| 5,584,830 A | 12/1996 | Ladd |
| 5,591,125 A | 1/1997 | Edwards et al. |
| 5,595,183 A | 1/1997 | Swanson et al. |
| 5,598,848 A | 2/1997 | Swanson et al. |
| 5,599,295 A | 2/1997 | Rosen et al. |
| 5,601,088 A | 2/1997 | Swanson et al. |
| 5,605,157 A | 2/1997 | Panescu et al. |
| 5,609,157 A | 3/1997 | Panescu et al. |
| 5,616,268 A | 4/1997 | Carr |
| 5,624,392 A | 4/1997 | Saab |
| 5,630,425 A | 5/1997 | Panescu et al. |
| 5,643,197 A | 7/1997 | Brucker et al. |
| 5,647,870 A | 7/1997 | Kordis et al. |
| 5,651,780 A | 7/1997 | Jackson et al. |
| 5,656,030 A | 8/1997 | Hunjan et al. |
| 5,658,278 A | 8/1997 | Imran et al. |
| 5,662,110 A | 9/1997 | Carr |
| 5,667,488 A | 9/1997 | Lundquist et al. |
| 5,672,174 A | 9/1997 | Gough et al. |
| 5,673,704 A | 10/1997 | Marchlinski et al. |
| 5,674,191 A | 10/1997 | Edwards et al. |
| 5,683,381 A | 11/1997 | Carr et al. |
| 5,683,382 A | 11/1997 | Lenihan et al. |
| 5,683,384 A | 11/1997 | Gough et al. |
| 5,685,839 A | 11/1997 | Edwards et al. |
| 5,685,878 A | 11/1997 | Falwell et al. |
| 5,688,050 A | 11/1997 | Sterzer et al. |
| 5,688,266 A | 11/1997 | Edwards et al. |
| 5,688,267 A | 11/1997 | Panescu et al. |
| 5,690,614 A | 11/1997 | Carr et al. |
| 5,702,386 A | 12/1997 | Stern et al. |
| 5,707,369 A | 1/1998 | Vaitekunas et al. |
| 5,711,305 A | 1/1998 | Swanson et al. |
| 5,712,047 A | 1/1998 | Aso et al. |
| 5,715,832 A | 2/1998 | Koblish et al. |
| 5,718,701 A | 2/1998 | Shai et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,735,847 A | 4/1998 | Gough et al. |
| 5,740,808 A | 4/1998 | Panescu et al. |
| 5,743,903 A | 4/1998 | Stern et al. |
| 5,752,518 A | 5/1998 | McGee et al. |
| 5,755,715 A | 5/1998 | Stern et al. |
| 5,762,786 A | 6/1998 | Oelbermann |
| 5,769,846 A | 6/1998 | Edwards et al. |
| 5,769,847 A | 6/1998 | Panescu et al. |
| 5,779,635 A | 7/1998 | Carr |
| 5,779,646 A | 7/1998 | Koblish et al. |
| 5,782,827 A | 7/1998 | Gough et al. |
| 5,782,828 A | 7/1998 | Chen et al. |
| 5,782,897 A | 7/1998 | Carr |
| 5,792,064 A | 8/1998 | Panescu et al. |
| 5,792,140 A | 8/1998 | Tu et al. |
| 5,795,303 A | 8/1998 | Swanson et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,432 A | 9/1998 | Swanson |
| 5,807,309 A | 9/1998 | Lundquist et al. |
| 5,807,395 A | 9/1998 | Mulier et al. |
| 5,810,802 A | 9/1998 | Panescu et al. |
| 5,810,804 A | 9/1998 | Gough et al. |
| 5,823,955 A | 10/1998 | Kuck et al. |
| 5,827,277 A | 10/1998 | Edwards |
| 5,830,213 A | 11/1998 | Panescu et al. |
| 5,833,621 A | 11/1998 | Panescu et al. |
| 5,833,688 A | 11/1998 | Sieben et al. |
| 5,836,874 A | 11/1998 | Swanson et al. |
| 5,836,947 A | 11/1998 | Fleischman et al. |

(56) References Cited

U.S. PATENT DOCUMENTS

| | | |
|---|---|---|
| 5,836,990 A | 11/1998 | Li |
| 5,837,001 A | 11/1998 | Mackey |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,849,028 A | 12/1998 | Chen |
| 5,853,409 A | 12/1998 | Swanson et al. |
| 5,853,411 A | 12/1998 | Whayne et al. |
| 5,863,290 A | 1/1999 | Gough et al. |
| 5,865,800 A | 2/1999 | Mirarchi et al. |
| 5,868,736 A | 2/1999 | Swanson et al. |
| 5,868,743 A | 2/1999 | Saul et al. |
| 5,871,483 A | 2/1999 | Jackson et al. |
| 5,876,336 A | 3/1999 | Swanson et al. |
| 5,876,340 A | 3/1999 | Tu et al. |
| 5,879,348 A | 3/1999 | Owens et al. |
| 5,879,349 A | 3/1999 | Edwards |
| 5,891,136 A | 4/1999 | McGee et al. |
| 5,893,885 A | 4/1999 | Webster, Jr. |
| 5,897,552 A | 4/1999 | Edwards et al. |
| 5,904,651 A | 5/1999 | Swanson et al. |
| 5,904,680 A | 5/1999 | Kordis et al. |
| 5,904,709 A | 5/1999 | Arndt et al. |
| 5,906,590 A | 5/1999 | Hunjan et al. |
| 5,906,614 A | 5/1999 | Stern et al. |
| 5,908,445 A | 6/1999 | Whayne et al. |
| 5,910,129 A | 6/1999 | Koblish et al. |
| 5,911,739 A | 6/1999 | Kordis et al. |
| 5,913,856 A | 6/1999 | Chia et al. |
| 5,916,163 A | 6/1999 | Panescu et al. |
| 5,919,218 A | 7/1999 | Carr |
| 5,925,038 A | 7/1999 | Panescu et al. |
| 5,928,228 A | 7/1999 | Kordis et al. |
| 5,928,229 A | 7/1999 | Gough et al. |
| 5,933,672 A | 8/1999 | Huang |
| 5,935,063 A | 8/1999 | Nguyen |
| 5,935,079 A | 8/1999 | Swanson et al. |
| 5,935,124 A | 8/1999 | Klumb et al. |
| 5,938,658 A | 8/1999 | Tu |
| 5,938,659 A | 8/1999 | Tu et al. |
| 5,941,251 A | 8/1999 | Panescu et al. |
| 5,948,009 A | 9/1999 | Tu |
| 5,954,661 A | 9/1999 | Greenspon et al. |
| 5,954,662 A | 9/1999 | Swanson et al. |
| 5,954,719 A | 9/1999 | Chen et al. |
| 5,957,863 A | 9/1999 | Koblish et al. |
| 5,957,922 A | 9/1999 | Imran |
| 5,957,961 A | 9/1999 | Maguire et al. |
| 5,961,513 A | 10/1999 | Swanson et al. |
| 5,964,727 A | 10/1999 | Edwards et al. |
| 5,967,976 A | 10/1999 | Larsen et al. |
| 5,968,040 A | 10/1999 | Swanson et al. |
| 5,971,980 A | 10/1999 | Sherman |
| 5,974,343 A | 10/1999 | Brevard et al. |
| 5,980,517 A | 11/1999 | Gough |
| 5,983,124 A | 11/1999 | Carr |
| 5,991,650 A | 11/1999 | Swanson et al. |
| 5,992,419 A | 11/1999 | Sterzer et al. |
| 5,997,534 A | 12/1999 | Tu et al. |
| 6,006,123 A | 12/1999 | Nguyen et al. |
| 6,009,351 A | 12/1999 | Flachman |
| 6,014,581 A | 1/2000 | Whayne et al. |
| 6,014,590 A | 1/2000 | Whayne et al. |
| 6,022,346 A | 2/2000 | Panescu et al. |
| 6,030,379 A | 2/2000 | Panescu et al. |
| 6,030,382 A | 2/2000 | Fleischman et al. |
| 6,032,061 A | 2/2000 | Koblish |
| 6,035,226 A | 3/2000 | Panescu |
| 6,047,218 A | 4/2000 | Whayne et al. |
| 6,048,329 A | 4/2000 | Thompson et al. |
| 6,049,732 A | 4/2000 | Panescu et al. |
| 6,053,912 A | 4/2000 | Panescu et al. |
| 6,056,745 A | 5/2000 | Panescu et al. |
| 6,059,780 A | 5/2000 | Gough et al. |
| 6,063,078 A | 5/2000 | Wittkampf |
| 6,066,136 A | 5/2000 | Geistert |
| 6,070,094 A | 5/2000 | Swanson et al. |
| 6,071,278 A | 6/2000 | Panescu et al. |
| 6,076,012 A | 6/2000 | Swanson et al. |
| 6,080,150 A | 6/2000 | Gough |
| 6,083,222 A | 7/2000 | Klein et al. |
| 6,086,532 A | 7/2000 | Panescu et al. |
| 6,090,105 A | 7/2000 | Zepeda et al. |
| 6,095,150 A | 8/2000 | Panescu et al. |
| 6,097,976 A | 8/2000 | Yang et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,113,593 A | 9/2000 | Tu et al. |
| 6,115,626 A | 9/2000 | Whayne et al. |
| 6,123,702 A | 9/2000 | Swanson et al. |
| 6,123,703 A | 9/2000 | Tu et al. |
| 6,129,669 A | 10/2000 | Panescu et al. |
| 6,129,724 A | 10/2000 | Fleischman et al. |
| 6,132,425 A | 10/2000 | Gough |
| 6,142,994 A | 11/2000 | Swanson et al. |
| 6,146,359 A | 11/2000 | Carr et al. |
| 6,162,184 A | 12/2000 | Swanson et al. |
| 6,165,169 A | 12/2000 | Panescu et al. |
| 6,171,275 B1 | 1/2001 | Webster, Jr. |
| 6,171,306 B1 | 1/2001 | Swanson et al. |
| 6,179,835 B1 | 1/2001 | Panescu et al. |
| 6,183,468 B1 | 2/2001 | Swanson et al. |
| 6,188,924 B1 | 2/2001 | Swanson et al. |
| 6,192,266 B1 | 2/2001 | Dupree et al. |
| 6,193,713 B1 | 2/2001 | Geistert et al. |
| 6,197,021 B1 | 3/2001 | Panescu et al. |
| 6,206,831 B1 | 3/2001 | Suorsa et al. |
| 6,210,367 B1 | 4/2001 | Carr |
| 6,210,406 B1 | 4/2001 | Webster |
| 6,216,043 B1 | 4/2001 | Swanson et al. |
| 6,217,528 B1 | 4/2001 | Koblish et al. |
| 6,217,573 B1 | 4/2001 | Webster |
| 6,217,574 B1 | 4/2001 | Webster |
| 6,217,576 B1 | 4/2001 | Tu et al. |
| 6,221,013 B1 | 4/2001 | Panescu et al. |
| 6,230,060 B1 | 5/2001 | Mawhinney |
| 6,235,022 B1 | 5/2001 | Hallock et al. |
| 6,235,023 B1 | 5/2001 | Lee et al. |
| 6,238,389 B1 | 5/2001 | Paddock et al. |
| 6,245,061 B1 | 6/2001 | Panescu et al. |
| 6,245,065 B1 | 6/2001 | Panescu et al. |
| 6,251,107 B1 | 6/2001 | Schaer |
| 6,256,525 B1 | 7/2001 | Yang et al. |
| 6,256,540 B1 | 7/2001 | Panescu et al. |
| 6,259,941 B1 | 7/2001 | Chia et al. |
| 6,277,113 B1 | 8/2001 | Berube |
| 6,283,962 B1 | 9/2001 | Tu et al. |
| 6,289,239 B1 | 9/2001 | Panescu et al. |
| 6,293,943 B1 | 9/2001 | Panescu et al. |
| 6,309,385 B1 | 10/2001 | Simpson |
| 6,330,473 B1 | 12/2001 | Swanson et al. |
| 6,346,104 B2 | 2/2002 | Daly et al. |
| 6,350,262 B1 | 2/2002 | Ashley |
| 6,352,534 B1 | 3/2002 | Paddock et al. |
| 6,353,751 B1 | 3/2002 | Swanson et al. |
| 6,356,790 B1 | 3/2002 | Maguire et al. |
| 6,357,447 B1 | 3/2002 | Swanson et al. |
| 6,364,876 B1 | 4/2002 | Erb et al. |
| 6,370,435 B2 | 4/2002 | Panescu et al. |
| 6,371,955 B1 | 4/2002 | Fuimaono et al. |
| 6,389,311 B1 | 5/2002 | Whayne et al. |
| 6,391,024 B1 | 5/2002 | Sun et al. |
| 6,402,739 B1 | 6/2002 | Neev |
| 6,402,742 B1 | 6/2002 | Blewett et al. |
| 6,405,067 B1 | 6/2002 | Mest et al. |
| 6,423,057 B1 | 7/2002 | He et al. |
| 6,424,869 B1 | 7/2002 | Carr et al. |
| 6,425,895 B1 | 7/2002 | Swanson et al. |
| 6,428,536 B2 | 8/2002 | Panescu et al. |
| 6,440,129 B1 | 8/2002 | Simpson |

(56) References Cited

U.S. PATENT DOCUMENTS

| | | |
|---|---|---|
| 6,445,957 B1 | 9/2002 | Bolmsjo |
| 6,456,864 B1 | 9/2002 | Swanson et al. |
| 6,458,123 B1 | 10/2002 | Brucker et al. |
| 6,463,331 B1 | 10/2002 | Edwards |
| 6,464,700 B1 | 10/2002 | Koblish et al. |
| 6,468,272 B1 | 10/2002 | Koblish et al. |
| 6,470,219 B1 | 10/2002 | Edwards et al. |
| 6,471,699 B1 | 10/2002 | Fleischman et al. |
| 6,477,396 B1 | 11/2002 | Mest et al. |
| 6,477,426 B1 | 11/2002 | Fenn et al. |
| 6,482,203 B2 | 11/2002 | Paddock et al. |
| 6,487,441 B1 | 11/2002 | Swanson et al. |
| 6,488,679 B1 | 12/2002 | Swanson et al. |
| 6,490,488 B1 | 12/2002 | Rudie et al. |
| 6,494,880 B1 | 12/2002 | Swanson et al. |
| 6,496,738 B2 | 12/2002 | Carr |
| 6,500,172 B2 | 12/2002 | Panescu et al. |
| 6,500,175 B1 | 12/2002 | Gough et al. |
| 6,508,765 B2 | 1/2003 | Suorsa et al. |
| 6,511,478 B1 | 1/2003 | Burnside et al. |
| 6,514,249 B1 | 2/2003 | Maguire et al. |
| 6,514,250 B1 | 2/2003 | Jahns et al. |
| 6,516,807 B1 | 2/2003 | Panescu et al. |
| 6,522,913 B2 | 2/2003 | Swanson et al. |
| 6,522,930 B1 | 2/2003 | Schaer et al. |
| 6,522,931 B2 | 2/2003 | Manker et al. |
| 6,529,756 B1 | 3/2003 | Phan et al. |
| 6,537,272 B2 | 3/2003 | Christopherson et al. |
| 6,542,773 B2 | 4/2003 | Dupree et al. |
| 6,542,781 B1 | 4/2003 | Koblish et al. |
| 6,565,511 B2 | 5/2003 | Panescu et al. |
| 6,577,902 B1 | 6/2003 | Laufer et al. |
| 6,579,288 B1 | 6/2003 | Swanson et al. |
| 6,582,425 B2 | 6/2003 | Simpson |
| 6,584,360 B2 | 6/2003 | Francischelli et al. |
| 6,587,732 B1 | 7/2003 | Carr |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,610,055 B1 | 8/2003 | Swanson et al. |
| 6,611,699 B2 | 8/2003 | Messing |
| 6,613,046 B1 | 9/2003 | Jenkins et al. |
| 6,615,073 B1 | 9/2003 | Panescu et al. |
| 6,616,657 B2 | 9/2003 | Simpson et al. |
| 6,625,482 B1 | 9/2003 | Panescu et al. |
| 6,632,221 B1 | 10/2003 | Edwards et al. |
| 6,632,222 B1 | 10/2003 | Edwards et al. |
| 6,635,056 B2 | 10/2003 | Kadhiresan et al. |
| 6,645,200 B1 | 11/2003 | Koblish et al. |
| 6,652,513 B2 | 11/2003 | Panescu et al. |
| 6,652,516 B1 | 11/2003 | Gough |
| 6,658,279 B2 | 12/2003 | Swanson et al. |
| 6,668,198 B2 | 12/2003 | Swanson et al. |
| 6,669,692 B1 | 12/2003 | Nelson et al. |
| 6,685,702 B2 | 2/2004 | Quijano et al. |
| 6,689,127 B1 | 2/2004 | Gough et al. |
| 6,692,490 B1 | 2/2004 | Edwards |
| 6,699,241 B2 | 3/2004 | Rappaport et al. |
| 6,706,038 B2 | 3/2004 | Francischelli et al. |
| 6,711,444 B2 | 3/2004 | Koblish |
| 6,735,465 B2 | 5/2004 | Panescu |
| 6,736,811 B2 | 5/2004 | Panescu et al. |
| 6,740,040 B1 | 5/2004 | Mandrusov et al. |
| 6,740,083 B2 | 5/2004 | Messing |
| 6,743,197 B1 | 6/2004 | Edwards |
| 6,743,225 B2 | 6/2004 | Sanchez et al. |
| 6,745,080 B2 | 6/2004 | Koblish |
| 6,746,401 B2 | 6/2004 | Panescu |
| 6,752,804 B2 | 6/2004 | Simpson et al. |
| 6,752,805 B2 | 6/2004 | Maguire et al. |
| 6,770,070 B1 | 8/2004 | Balbierz |
| 6,773,433 B2 | 8/2004 | Stewart et al. |
| 6,786,905 B2 | 9/2004 | Swanson et al. |
| 6,788,969 B2 | 9/2004 | Dupree et al. |
| 6,788,977 B2 | 9/2004 | Fenn et al. |
| 6,790,206 B2 | 9/2004 | Panescu |
| 6,805,129 B1 | 10/2004 | Pless et al. |
| 6,814,730 B2 | 11/2004 | Li |
| 6,823,216 B1 | 11/2004 | Salomir et al. |
| 6,824,515 B2 | 11/2004 | Suorsa et al. |
| 6,827,715 B2 | 12/2004 | Francischelli et al. |
| 6,837,885 B2 | 1/2005 | Koblish et al. |
| 6,840,936 B2 | 1/2005 | Sliwa, Jr. et al. |
| 6,847,848 B2 | 1/2005 | Sterzer et al. |
| 6,849,073 B2 | 2/2005 | Hoey et al. |
| 6,852,120 B1 | 2/2005 | Fuimaono |
| 6,887,238 B2 | 5/2005 | Jahns et al. |
| 6,888,141 B2 | 5/2005 | Carr |
| 6,895,267 B2 | 5/2005 | Panescu et al. |
| 6,904,303 B2 | 6/2005 | Phan et al. |
| 6,905,495 B1 | 6/2005 | Fuimaono et al. |
| 6,917,834 B2 | 7/2005 | Koblish et al. |
| 6,932,776 B2 | 8/2005 | Carr |
| 6,932,813 B2 | 8/2005 | Thompson et al. |
| 6,936,047 B2 | 8/2005 | Nasab et al. |
| 6,942,661 B2 | 9/2005 | Swanson |
| 6,949,095 B2 | 9/2005 | Vaska et al. |
| 6,953,460 B2 | 10/2005 | Maguire et al. |
| 6,958,075 B2 | 10/2005 | Mon et al. |
| 6,960,205 B2 | 11/2005 | Jahns et al. |
| 6,960,207 B2 | 11/2005 | Vanney et al. |
| 6,974,455 B2 | 12/2005 | Garabedian et al. |
| 6,976,492 B2 | 12/2005 | Ingle et al. |
| 6,979,329 B2 | 12/2005 | Burnside et al. |
| 6,984,232 B2 | 1/2006 | Vanney et al. |
| 6,986,769 B2 | 1/2006 | Nelson et al. |
| 7,001,383 B2 | 2/2006 | Keidar |
| 7,008,417 B2 | 3/2006 | Eick |
| 7,029,470 B2 | 4/2006 | Francischelli et al. |
| 7,052,492 B2 | 5/2006 | Swanson et al. |
| 7,101,387 B2 | 9/2006 | Garabedian et al. |
| 7,150,744 B2 | 12/2006 | Edwards et al. |
| 7,151,964 B2 | 12/2006 | Desai et al. |
| 7,160,296 B2 | 1/2007 | Pearson et al. |
| 7,163,537 B2 | 1/2007 | Lee et al. |
| 7,166,075 B2 | 1/2007 | Varghese et al. |
| 7,175,619 B2 | 2/2007 | Koblish et al. |
| 7,175,734 B2 | 2/2007 | Stewart et al. |
| 7,184,811 B2 | 2/2007 | Phan et al. |
| 7,186,250 B2 | 3/2007 | Koblish et al. |
| 7,194,294 B2 | 3/2007 | Panescu et al. |
| 7,197,356 B2 | 3/2007 | Carr |
| 7,229,437 B2 | 6/2007 | Johnson et al. |
| 7,238,184 B2 | 7/2007 | Megerman et al. |
| 7,252,664 B2 | 8/2007 | Nasab et al. |
| 7,263,398 B2 | 8/2007 | Carr |
| 7,276,061 B2 | 10/2007 | Schaer et al. |
| 7,285,116 B2 | 10/2007 | de la Rama et al. |
| 7,303,558 B2 | 12/2007 | Swanson |
| 7,306,593 B2 | 12/2007 | Keidar et al. |
| 7,326,208 B2 | 2/2008 | Vanney et al. |
| 7,326,235 B2 | 2/2008 | Edwards |
| 7,331,960 B2 | 2/2008 | Schaer |
| 7,338,486 B2 | 3/2008 | Sliwa et al. |
| 7,344,533 B2 | 3/2008 | Pearson et al. |
| 7,364,546 B2 | 4/2008 | Panescu et al. |
| 7,364,578 B2 | 4/2008 | Francischelli et al. |
| 7,367,972 B2 | 5/2008 | Francischelli et al. |
| 7,371,233 B2 | 5/2008 | Swanson et al. |
| 7,371,235 B2 | 5/2008 | Thompson et al. |
| 7,435,248 B2 | 10/2008 | Taimisto et al. |
| 7,474,909 B2 | 1/2009 | Phan et al. |
| 7,565,208 B2 | 7/2009 | Harris et al. |
| 7,582,050 B2 | 9/2009 | Schlorff et al. |
| 7,582,084 B2 | 9/2009 | Swanson et al. |
| 7,588,568 B2 | 9/2009 | Fuimaono et al. |
| 7,588,658 B2 | 9/2009 | Yamamoto et al. |
| 7,623,899 B2 | 11/2009 | Worley et al. |
| 7,628,788 B2 | 12/2009 | Datta |
| 7,662,152 B2 | 2/2010 | Sharareh et al. |
| 7,669,309 B2 | 3/2010 | Johnson et al. |
| 7,670,336 B2 | 3/2010 | Young et al. |
| 7,676,264 B1 | 3/2010 | Pillai et al. |

(56) References Cited

U.S. PATENT DOCUMENTS

| | | |
|---|---|---|
| 7,678,104 B2 | 3/2010 | Keidar |
| 7,699,829 B2 | 4/2010 | Harris et al. |
| 7,699,841 B2 | 4/2010 | Carr |
| 7,715,926 B2 | 5/2010 | Boser et al. |
| 7,727,230 B2 | 6/2010 | Fuimaono et al. |
| 7,734,330 B2 | 6/2010 | Carr |
| 7,761,148 B2 | 7/2010 | Fuimaono et al. |
| 7,764,994 B2 | 7/2010 | Fuimaono et al. |
| 7,766,693 B2 | 8/2010 | Sartor et al. |
| 7,766,907 B2 | 8/2010 | Dando et al. |
| 7,769,469 B2 | 8/2010 | Carr et al. |
| 7,771,418 B2 | 8/2010 | Chopra et al. |
| 7,771,420 B2 | 8/2010 | Butty et al. |
| 7,774,039 B2 | 8/2010 | Koblish |
| 7,776,034 B2 | 8/2010 | Kampa |
| 7,794,404 B1 | 9/2010 | Gutfinger et al. |
| 7,794,460 B2 | 9/2010 | Mulier et al. |
| 7,811,313 B2 | 10/2010 | Mon et al. |
| 7,815,635 B2 | 10/2010 | Wittkampf et al. |
| 7,819,862 B2 | 10/2010 | Pachon Mateos et al. |
| 7,819,866 B2 | 10/2010 | Bednarek |
| 7,824,399 B2 | 11/2010 | Francischelli et al. |
| 7,826,904 B2 | 11/2010 | Appling et al. |
| 7,833,220 B2 | 11/2010 | Mon et al. |
| 7,837,720 B2 | 11/2010 | Mon |
| 7,857,809 B2 | 12/2010 | Drysen |
| 7,857,810 B2 | 12/2010 | Wang et al. |
| 7,862,563 B1 | 1/2011 | Cosman et al. |
| 7,867,227 B2 | 1/2011 | Slater |
| 7,879,029 B2 | 2/2011 | Jimenez |
| 7,914,528 B2 | 3/2011 | Wang et al. |
| 7,918,850 B2 | 4/2011 | Govari et al. |
| 7,918,851 B2 | 4/2011 | Webster, Jr. et al. |
| 7,925,341 B2 | 4/2011 | Fuimaono |
| 7,925,349 B1 | 4/2011 | Wong et al. |
| 7,927,328 B2 | 4/2011 | Orszulak et al. |
| 7,933,660 B2 | 4/2011 | Carr |
| 7,938,828 B2 | 5/2011 | Koblish |
| 7,945,326 B1 | 5/2011 | Wong et al. |
| 7,946,995 B1 | 5/2011 | Koh et al. |
| 7,955,369 B2 | 6/2011 | Thompson et al. |
| 7,957,813 B1 | 6/2011 | Persson |
| 7,959,628 B2 | 6/2011 | Schaer et al. |
| 7,959,630 B2 | 6/2011 | Taimisto et al. |
| 7,963,925 B1 | 6/2011 | Schecter |
| 7,967,817 B2 | 6/2011 | Anderson et al. |
| 7,976,537 B2 | 7/2011 | Lieber et al. |
| 7,989,741 B2 | 8/2011 | Carr |
| 7,996,078 B2 | 8/2011 | Paul et al. |
| 7,998,140 B2 | 8/2011 | McClurken et al. |
| 7,998,141 B2 | 8/2011 | Wttkampf et al. |
| 8,002,770 B2 | 8/2011 | Swanson et al. |
| 8,007,497 B2 | 8/2011 | Young et al. |
| 8,010,196 B1 | 8/2011 | Wong et al. |
| 8,011,055 B2 | 9/2011 | Lesley |
| 8,012,150 B2 | 9/2011 | Wham et al. |
| 8,019,419 B1 | 9/2011 | Panescu et al. |
| 8,032,218 B2 | 10/2011 | Wong et al. |
| 8,034,050 B2 | 10/2011 | Sharareh et al. |
| 8,034,052 B2 | 10/2011 | Podhajsky |
| 8,038,670 B2 | 10/2011 | McClurken |
| 8,048,070 B2 | 11/2011 | O'Brien et al. |
| 8,052,680 B2 | 11/2011 | Hassett et al. |
| 8,052,684 B2 | 11/2011 | Wang et al. |
| 8,062,228 B2 | 11/2011 | Carr |
| 8,065,005 B1 | 11/2011 | Wong et al. |
| 8,083,736 B2 | 12/2011 | McClurken et al. |
| 8,100,895 B2 | 1/2012 | Panos et al. |
| 8,104,956 B2 | 1/2012 | Blaha |
| 8,118,809 B2 | 2/2012 | Paul et al. |
| 8,123,745 B2 | 2/2012 | Beeckler et al. |
| 8,128,617 B2 | 3/2012 | Bencini et al. |
| 8,128,621 B2 | 3/2012 | Wang et al. |
| 8,133,220 B2 | 3/2012 | Lee et al. |
| 8,145,289 B2 | 3/2012 | Calabro' et al. |
| 8,152,801 B2 | 4/2012 | Goldberg et al. |
| 8,157,796 B2 | 4/2012 | Collins et al. |
| 8,160,693 B2 | 4/2012 | Fuimaono |
| 8,175,680 B2 | 5/2012 | Panescu |
| 8,192,424 B2 | 6/2012 | Woloszko |
| 8,202,224 B2 | 6/2012 | Gutfinger et al. |
| 8,206,380 B2 | 6/2012 | Lenihan et al. |
| 8,206,383 B2 | 6/2012 | Hauck et al. |
| 8,206,385 B2 | 6/2012 | Stangenes et al. |
| 8,208,999 B2 | 6/2012 | Wenzel et al. |
| 8,211,099 B2 | 7/2012 | Buysse et al. |
| 8,216,216 B2 | 7/2012 | Warnking et al. |
| 8,221,408 B2 | 7/2012 | Johnson et al. |
| 8,221,413 B2 | 7/2012 | Mon et al. |
| 8,221,414 B2 | 7/2012 | Mon et al. |
| 8,224,455 B2 | 7/2012 | Mon et al. |
| 8,226,645 B2 | 7/2012 | Harrington et al. |
| 8,229,538 B2 | 7/2012 | Koblish |
| 8,256,428 B2 | 9/2012 | Hindricks et al. |
| 8,262,652 B2 | 9/2012 | Podhajsky |
| 8,262,653 B2 | 9/2012 | Plaza |
| 8,265,747 B2 | 9/2012 | Rittman, III et al. |
| 8,267,926 B2 | 9/2012 | Paul et al. |
| 8,267,929 B2 | 9/2012 | Wham et al. |
| 8,267,932 B2 | 9/2012 | Baxter et al. |
| 8,273,082 B2 | 9/2012 | Wang et al. |
| 8,280,511 B2 | 10/2012 | Zhao et al. |
| 8,287,532 B2 | 10/2012 | Carroll et al. |
| 8,287,533 B2 | 10/2012 | Wittkampf |
| 8,290,578 B2 | 10/2012 | Schneider |
| 8,298,223 B2 | 10/2012 | Wham et al. |
| 8,298,227 B2 | 10/2012 | Leo et al. |
| 8,303,172 B2 | 11/2012 | Zei et al. |
| 8,303,580 B2 | 11/2012 | Wham et al. |
| 8,306,623 B2 | 11/2012 | Wong et al. |
| 8,308,719 B2 | 11/2012 | Sliwa et al. |
| 8,317,783 B2 | 11/2012 | Cao et al. |
| 8,321,019 B2 | 11/2012 | Esch et al. |
| 8,333,759 B2 | 12/2012 | Podhajsky |
| 8,333,762 B2 | 12/2012 | Mest et al. |
| 8,348,937 B2 | 1/2013 | Wang et al. |
| 8,359,092 B2 | 1/2013 | Hayam et al. |
| 8,369,922 B2 | 2/2013 | Paul et al. |
| 8,372,066 B2 | 2/2013 | Manwaring et al. |
| 8,374,670 B2 | 2/2013 | Selkee |
| 8,374,702 B2 | 2/2013 | Mon et al. |
| 8,377,052 B2 | 2/2013 | Manwaring et al. |
| 8,377,054 B2 | 2/2013 | Gilbert |
| 8,380,275 B2 | 2/2013 | Kim et al. |
| 8,386,049 B2 | 2/2013 | Persson et al. |
| 8,394,093 B2 | 3/2013 | Wang et al. |
| 8,398,623 B2 | 3/2013 | Warnking et al. |
| 8,403,925 B2 | 3/2013 | Miller et al. |
| 8,406,866 B2 | 3/2013 | Deno et al. |
| 8,409,191 B2 | 4/2013 | Avitall et al. |
| 8,409,192 B2 | 4/2013 | Asirvatham et al. |
| 8,414,570 B2 | 4/2013 | Turner et al. |
| 8,414,579 B2 | 4/2013 | Kim et al. |
| 8,419,725 B2 | 4/2013 | Haemmerich et al. |
| 8,423,115 B2 | 4/2013 | Koblish |
| 8,440,949 B2 | 5/2013 | Carr |
| 8,442,613 B2 | 5/2013 | Kim et al. |
| 8,444,637 B2 | 5/2013 | Podmore et al. |
| 8,449,535 B2 | 5/2013 | Deno et al. |
| 8,449,537 B2 | 5/2013 | Cao et al. |
| 8,449,539 B2 | 5/2013 | Wang et al. |
| 8,460,285 B2 | 6/2013 | Wang et al. |
| 8,473,023 B2 | 6/2013 | Worley et al. |
| 8,475,448 B2 | 7/2013 | Sharareh et al. |
| 8,475,450 B2 | 7/2013 | Govari et al. |
| 8,480,663 B2 | 7/2013 | Ingle et al. |
| 8,480,666 B2 | 7/2013 | Buysse et al. |
| 8,486,065 B2 | 7/2013 | Lee et al. |
| 8,491,578 B2 | 7/2013 | Manwaring et al. |
| 8,504,152 B2 | 8/2013 | Wenzel et al. |
| 8,504,153 B2 | 8/2013 | Wenzel et al. |
| 8,515,554 B2 | 8/2013 | Carr |
| 8,517,999 B2 | 8/2013 | Pappone et al. |
| 8,523,851 B2 | 9/2013 | Manwaring et al. |

(56) References Cited

U.S. PATENT DOCUMENTS

| | | |
|---|---|---|
| 8,523,852 B2 | 9/2013 | Manwaring et al. |
| 8,535,303 B2 | 9/2013 | Avitall et al. |
| 8,545,409 B2 | 10/2013 | Sliwa et al. |
| 8,554,333 B2 | 10/2013 | Wu et al. |
| 8,556,893 B2 | 10/2013 | Potter |
| 8,560,086 B2 | 10/2013 | Just et al. |
| 8,562,600 B2 | 10/2013 | Kirkpatrick et al. |
| 8,568,402 B2 | 10/2013 | Buysse et al. |
| 8,574,166 B2 | 11/2013 | Carr |
| 8,600,472 B2 | 12/2013 | Govari et al. |
| 8,600,497 B1 | 12/2013 | Yang et al. |
| 8,603,084 B2 | 12/2013 | Fish et al. |
| 8,603,085 B2 | 12/2013 | Jimenez |
| 8,628,520 B2 | 1/2014 | Sharareh et al. |
| 8,632,533 B2 | 1/2014 | Greeley et al. |
| 8,636,729 B2 | 1/2014 | Esch et al. |
| 8,641,708 B2 | 2/2014 | Govari et al. |
| 8,657,814 B2 | 2/2014 | Werneth et al. |
| 8,663,122 B2 | 3/2014 | Schecter |
| 8,668,686 B2 | 3/2014 | Govari et al. |
| 8,679,109 B2 | 3/2014 | Paul et al. |
| 8,690,870 B2 | 4/2014 | Wang et al. |
| 8,696,659 B2 | 4/2014 | Marion |
| 8,700,120 B2 | 4/2014 | Koblish |
| 8,702,690 B2 | 4/2014 | Paul et al. |
| 8,702,693 B2 | 4/2014 | Subramaniam et al. |
| 8,712,519 B1 | 4/2014 | Panescu et al. |
| 8,721,634 B2 | 5/2014 | Esch et al. |
| 8,721,636 B2 | 5/2014 | Vaska et al. |
| 8,725,228 B2 | 5/2014 | Koblish et al. |
| 8,728,074 B2 | 5/2014 | West et al. |
| 8,728,077 B2 | 5/2014 | Paul et al. |
| 8,731,631 B2 | 5/2014 | Kim et al. |
| 8,731,684 B2 | 5/2014 | Carr et al. |
| 8,734,442 B2 | 5/2014 | Cao et al. |
| 8,740,900 B2 | 6/2014 | Kim et al. |
| 8,755,860 B2 | 6/2014 | Paul et al. |
| 8,764,746 B2 | 7/2014 | Podmore et al. |
| 8,777,942 B2 | 7/2014 | Wu et al. |
| 8,784,414 B2 | 7/2014 | Avitall et al. |
| 8,792,958 B2 | 7/2014 | Kim et al. |
| 8,795,271 B2 | 8/2014 | Koblish et al. |
| 8,798,706 B2 | 8/2014 | Kim et al. |
| 8,814,824 B2 | 8/2014 | Kauphusman et al. |
| 8,814,857 B2 | 8/2014 | Christian |
| 8,834,388 B2 | 9/2014 | Sherman |
| 8,834,461 B2 | 9/2014 | Werneth et al. |
| 8,845,629 B2 | 9/2014 | Demarais et al. |
| 8,845,631 B2 | 9/2014 | Werneth et al. |
| 8,845,633 B2 | 9/2014 | Wang et al. |
| 8,858,548 B2 | 10/2014 | Asconeguy |
| 8,868,165 B1 | 10/2014 | Nabutovsky et al. |
| 8,876,817 B2 | 11/2014 | Avitall et al. |
| 8,876,819 B2 | 11/2014 | Tegg et al. |
| 8,882,755 B2 | 11/2014 | Leung et al. |
| 8,882,759 B2 | 11/2014 | Manley et al. |
| 8,882,761 B2 | 11/2014 | Desai |
| 8,894,642 B2 | 11/2014 | Gibson et al. |
| 8,900,225 B2 | 12/2014 | Bar-Tai et al. |
| 8,900,228 B2 | 12/2014 | Grunewald et al. |
| 8,906,010 B2 | 12/2014 | Edwards et al. |
| 8,920,415 B2 | 12/2014 | Govari |
| 8,926,605 B2 | 1/2015 | McCarthy et al. |
| 8,932,284 B2 | 1/2015 | McCarthy et al. |
| 8,934,953 B2 | 1/2015 | Carr et al. |
| 8,942,828 B1 | 1/2015 | Schecter |
| 8,945,015 B2 | 2/2015 | Rankin et al. |
| 8,945,117 B2 | 2/2015 | Bencini |
| 8,954,161 B2 | 2/2015 | McCarthy et al. |
| 8,956,304 B2 | 2/2015 | Schecter |
| 8,961,506 B2 | 2/2015 | McCarthy et al. |
| 8,968,299 B2 | 3/2015 | Kauphusman et al. |
| 8,974,454 B2 | 3/2015 | de la Rama et al. |
| 8,992,519 B2 | 3/2015 | Kim et al. |
| 8,998,890 B2 | 4/2015 | Paul et al. |
| 9,014,814 B2 | 4/2015 | McCarthy et al. |
| 9,023,030 B2 | 5/2015 | Koblish et al. |
| 9,050,069 B2 | 6/2015 | Lalonde et al. |
| 9,060,756 B2 | 6/2015 | Bencini et al. |
| 9,066,662 B2 | 6/2015 | Wenzel et al. |
| 9,066,725 B2 | 6/2015 | Christian |
| 9,089,339 B2 | 7/2015 | McDaniel |
| 9,089,340 B2 | 7/2015 | Hastings et al. |
| 9,095,349 B2 | 8/2015 | Fish et al. |
| 9,144,460 B2 | 9/2015 | Clark et al. |
| 9,173,586 B2 | 11/2015 | Deno et al. |
| 9,179,972 B2 | 11/2015 | Olson |
| 9,204,927 B2 | 12/2015 | Afonso et al. |
| 9,226,791 B2 | 1/2016 | McCarthy et al. |
| 9,226,793 B2 | 1/2016 | Jimenez |
| 9,254,163 B2 | 2/2016 | Paul et al. |
| 9,265,574 B2 | 2/2016 | Bar-Tai et al. |
| 9,271,782 B2 | 3/2016 | Paul et al. |
| 9,277,961 B2 | 3/2016 | Panescu et al. |
| 9,283,025 B2 | 3/2016 | Paul et al. |
| 9,283,026 B2 | 3/2016 | Paul et al. |
| 9,364,282 B2 | 6/2016 | Just et al. |
| 9,364,286 B2 | 6/2016 | Werneth et al. |
| 9,370,311 B2 | 6/2016 | Stewart et al. |
| 9,456,867 B2 | 10/2016 | Lawrence et al. |
| 9,474,458 B2 | 10/2016 | Clark et al. |
| 9,510,893 B2 | 12/2016 | Jimenez |
| 9,510,894 B2 | 12/2016 | Clark et al. |
| 9,510,905 B2 | 12/2016 | Panescu et al. |
| 9,517,103 B2 | 12/2016 | Panescu et al. |
| 9,522,036 B2 | 12/2016 | Panescu et al. |
| 9,522,037 B2 | 12/2016 | Panescu et al. |
| 9,592,092 B2 | 3/2017 | Panescu et al. |
| 9,636,164 B2 | 5/2017 | Panescu et al. |
| 2001/0001830 A1 | 5/2001 | Dobak et al. |
| 2001/0007927 A1 | 7/2001 | Koblish et al. |
| 2002/0004631 A1 | 1/2002 | Jenkins et al. |
| 2002/0022829 A1 | 2/2002 | Nagase et al. |
| 2002/0026185 A1 | 2/2002 | Gough |
| 2002/0040229 A1 | 4/2002 | Norman |
| 2002/0058870 A1 | 5/2002 | Panescu et al. |
| 2002/0065465 A1 | 5/2002 | Panescu et al. |
| 2002/0115941 A1 | 8/2002 | Whayne et al. |
| 2002/0128636 A1 | 9/2002 | Chin et al. |
| 2002/0128639 A1 | 9/2002 | Pless et al. |
| 2002/0128643 A1 | 9/2002 | Simpson et al. |
| 2002/0165529 A1 | 11/2002 | Danek |
| 2002/0169444 A1 | 11/2002 | Mest et al. |
| 2002/0183736 A1 | 12/2002 | Francischelli et al. |
| 2002/0193790 A1 | 12/2002 | Fleischman et al. |
| 2002/0198520 A1 | 12/2002 | Coen et al. |
| 2003/0014049 A1 | 1/2003 | Koblish et al. |
| 2003/0050557 A1 | 3/2003 | Susil et al. |
| 2003/0055470 A1 | 3/2003 | Mon et al. |
| 2003/0065322 A1 | 4/2003 | Panescu et al. |
| 2003/0069619 A1 | 4/2003 | Fenn et al. |
| 2003/0078509 A1 | 4/2003 | Panescu |
| 2003/0078573 A1 | 4/2003 | Truckai et al. |
| 2003/0088244 A1 | 5/2003 | Swanson et al. |
| 2003/0093067 A1 | 5/2003 | Panescu |
| 2003/0120171 A1 | 6/2003 | Diamantopoulos et al. |
| 2003/0153967 A1 | 8/2003 | Koblish et al. |
| 2003/0195406 A1 | 10/2003 | Jenkins et al. |
| 2003/0199817 A1 | 10/2003 | Thompson et al. |
| 2004/0044340 A1 | 3/2004 | Francischelli et al. |
| 2004/0054272 A1 | 3/2004 | Messing |
| 2004/0092806 A1 | 5/2004 | Sagon et al. |
| 2004/0097803 A1 | 5/2004 | Panescu |
| 2004/0138656 A1 | 7/2004 | Francischelli et al. |
| 2004/0147915 A1 | 7/2004 | Hasebe |
| 2004/0260278 A1 | 12/2004 | Anderson et al. |
| 2005/0015082 A1 | 1/2005 | O'Sullivan et al. |
| 2005/0033221 A1 | 2/2005 | Fiumaono |
| 2005/0059963 A1 | 3/2005 | Phan et al. |
| 2005/0143727 A1 | 6/2005 | Koblish et al. |
| 2005/0177151 A1 | 8/2005 | Coen et al. |
| 2005/0197657 A1 | 9/2005 | Goth et al. |
| 2005/0228370 A1 | 10/2005 | Sterzer et al. |
| 2005/0245949 A1 | 11/2005 | Goth et al. |

(56) References Cited

U.S. PATENT DOCUMENTS

| | | |
|---|---|---|
| 2005/0251125 A1 | 11/2005 | Pless et al. |
| 2006/0025758 A1 | 2/2006 | Strul et al. |
| 2006/0064083 A1 | 3/2006 | Khalaj et al. |
| 2006/0089688 A1 | 4/2006 | Panescu |
| 2006/0095032 A1 | 5/2006 | Jackson et al. |
| 2006/0135957 A1 | 6/2006 | Panescu |
| 2006/0167445 A1 | 7/2006 | Shafirstein |
| 2006/0184166 A1 | 8/2006 | Valle et al. |
| 2006/0184221 A1 | 8/2006 | Stewart et al. |
| 2006/0217701 A1 | 9/2006 | Young et al. |
| 2006/0247615 A1 | 11/2006 | McCullagh et al. |
| 2006/0253115 A1 | 11/2006 | Avitall et al. |
| 2006/0293731 A1 | 12/2006 | Rubinsky et al. |
| 2007/0032788 A1 | 2/2007 | Edwards et al. |
| 2007/0049925 A1 | 3/2007 | Phan et al. |
| 2007/0055227 A1 | 3/2007 | Khalaj et al. |
| 2007/0055326 A1 | 3/2007 | Farley et al. |
| 2007/0055328 A1 | 3/2007 | Mayse et al. |
| 2007/0066968 A1 | 3/2007 | Rahn |
| 2007/0066972 A1 | 3/2007 | Ormsby et al. |
| 2007/0073286 A1 | 3/2007 | Panescu et al. |
| 2007/0129720 A1 | 6/2007 | Demarais et al. |
| 2007/0135810 A1 | 6/2007 | Lee et al. |
| 2007/0149963 A1 | 6/2007 | Matsukuma et al. |
| 2007/0156048 A1 | 7/2007 | Panescu et al. |
| 2007/0156114 A1 | 7/2007 | Worley et al. |
| 2007/0179378 A1 | 8/2007 | Boese et al. |
| 2007/0185478 A1 | 8/2007 | Cosentino |
| 2007/0198007 A1 | 8/2007 | Govari et al. |
| 2007/0225697 A1 | 9/2007 | Shroff et al. |
| 2007/0244476 A1 | 10/2007 | Kochamba et al. |
| 2007/0244534 A1 | 10/2007 | Kochamba et al. |
| 2007/0299488 A1 | 12/2007 | Carr |
| 2008/0015563 A1 | 1/2008 | Hoey et al. |
| 2008/0015571 A1 | 1/2008 | Rubinsky et al. |
| 2008/0033300 A1 | 2/2008 | Hoang et al. |
| 2008/0077126 A1 | 3/2008 | Rashidi |
| 2008/0082091 A1 | 4/2008 | Rubtsov et al. |
| 2008/0161791 A1 | 7/2008 | Cao et al. |
| 2008/0161797 A1 | 7/2008 | Wang et al. |
| 2008/0172048 A1 | 7/2008 | Martin et al. |
| 2008/0177205 A1 | 7/2008 | Rama et al. |
| 2008/0243112 A1 | 10/2008 | De Neve |
| 2008/0243214 A1 | 10/2008 | Koblish |
| 2008/0249463 A1 | 10/2008 | Pappone et al. |
| 2008/0275440 A1 | 11/2008 | Kratoska et al. |
| 2008/0300589 A1 | 12/2008 | Paul et al. |
| 2008/0312521 A1 | 12/2008 | Solomon |
| 2009/0005768 A1 | 1/2009 | Sharareh et al. |
| 2009/0036882 A1 | 2/2009 | Webster et al. |
| 2009/0069808 A1 | 3/2009 | Pike, Jr. et al. |
| 2009/0076409 A1 | 3/2009 | Wu et al. |
| 2009/0093810 A1 | 4/2009 | Subramaniam et al. |
| 2009/0099560 A1 | 4/2009 | Rioux et al. |
| 2009/0118613 A1 | 5/2009 | Krugman et al. |
| 2009/0163916 A1 | 6/2009 | Paul et al. |
| 2009/0177111 A1 | 7/2009 | Miller et al. |
| 2009/0177193 A1 | 7/2009 | Wang et al. |
| 2009/0187183 A1 | 7/2009 | Epstein |
| 2009/0221999 A1 | 9/2009 | Shahidi |
| 2009/0248006 A1 | 10/2009 | Paulus et al. |
| 2009/0254083 A1 | 10/2009 | Wallace et al. |
| 2009/0275827 A1 | 11/2009 | Aiken et al. |
| 2009/0287201 A1 | 11/2009 | Lalonde et al. |
| 2009/0306641 A1 | 12/2009 | Govari et al. |
| 2009/0306643 A1 | 12/2009 | Pappone et al. |
| 2009/0312754 A1 | 12/2009 | Lenihan et al. |
| 2009/0312756 A1 | 12/2009 | Schlesinger et al. |
| 2010/0016848 A1 | 1/2010 | Desai |
| 2010/0023000 A1* | 1/2010 | Stevenson ............... A61N 1/05 607/116 |
| 2010/0030209 A1 | 2/2010 | Govari et al. |
| 2010/0049011 A1 | 2/2010 | Boese et al. |
| 2010/0057072 A1 | 3/2010 | Roman et al. |
| 2010/0057073 A1 | 3/2010 | Roman et al. |
| 2010/0057074 A1 | 3/2010 | Roman et al. |
| 2010/0057080 A1 | 3/2010 | West et al. |
| 2010/0076424 A1 | 3/2010 | Carr |
| 2010/0094271 A1 | 4/2010 | Ward et al. |
| 2010/0114087 A1 | 5/2010 | Edwards et al. |
| 2010/0114227 A1 | 5/2010 | Cholette |
| 2010/0137837 A1 | 6/2010 | Govari et al. |
| 2010/0137857 A1 | 6/2010 | Shroff et al. |
| 2010/0152724 A1 | 6/2010 | Marion et al. |
| 2010/0168570 A1 | 7/2010 | Sliwa et al. |
| 2010/0168571 A1 | 7/2010 | Savery et al. |
| 2010/0168620 A1 | 7/2010 | Klimovitch et al. |
| 2010/0174280 A1 | 7/2010 | Grimaldi |
| 2010/0185191 A1 | 7/2010 | Carr et al. |
| 2010/0198312 A1 | 8/2010 | Stevenson et al. |
| 2010/0204691 A1 | 8/2010 | Bencini |
| 2010/0211070 A1 | 8/2010 | Subramaniam et al. |
| 2010/0217255 A1 | 8/2010 | Greeley et al. |
| 2010/0222859 A1 | 9/2010 | Govari et al. |
| 2010/0286684 A1 | 11/2010 | Hata et al. |
| 2010/0286690 A1 | 11/2010 | Paul et al. |
| 2010/0298823 A1 | 11/2010 | Cao et al. |
| 2010/0331838 A1 | 12/2010 | Ibrahim et al. |
| 2011/0009857 A1 | 1/2011 | Subramaniam et al. |
| 2011/0022041 A1 | 1/2011 | Ingle et al. |
| 2011/0028821 A1 | 2/2011 | Bojovic et al. |
| 2011/0066147 A1 | 3/2011 | He et al. |
| 2011/0077498 A1 | 3/2011 | McDaniel |
| 2011/0105928 A1 | 5/2011 | Bojovic et al. |
| 2011/0112413 A1 | 5/2011 | Panescu et al. |
| 2011/0112414 A1 | 5/2011 | Panescu |
| 2011/0112415 A1 | 5/2011 | Bojovic et al. |
| 2011/0118726 A1 | 5/2011 | de la Rama et al. |
| 2011/0144479 A1 | 6/2011 | Hastings et al. |
| 2011/0144524 A1 | 6/2011 | Fish et al. |
| 2011/0144639 A1 | 6/2011 | Govari |
| 2011/0152853 A1 | 6/2011 | Manley et al. |
| 2011/0160726 A1 | 6/2011 | Ingle |
| 2011/0166472 A1 | 7/2011 | Björling et al. |
| 2011/0172658 A1 | 7/2011 | Gelbart et al. |
| 2011/0184300 A1 | 7/2011 | Shvilkin et al. |
| 2011/0184313 A1 | 7/2011 | Gianchandani et al. |
| 2011/0213356 A1 | 9/2011 | Wright et al. |
| 2011/0224573 A1 | 9/2011 | Bar-Tal et al. |
| 2011/0224664 A1 | 9/2011 | Bar-Tal et al. |
| 2011/0224667 A1 | 9/2011 | Koblish et al. |
| 2011/0257645 A1 | 10/2011 | Thompson et al. |
| 2011/0264000 A1 | 10/2011 | Paul et al. |
| 2011/0264011 A1 | 10/2011 | Wu et al. |
| 2011/0264089 A1 | 10/2011 | Zirkle et al. |
| 2011/0270244 A1 | 11/2011 | Clark et al. |
| 2011/0270246 A1 | 11/2011 | Clark et al. |
| 2011/0282250 A1 | 11/2011 | Fung et al. |
| 2011/0282342 A1 | 11/2011 | Leo et al. |
| 2011/0288544 A1 | 11/2011 | Verin et al. |
| 2011/0295247 A1 | 12/2011 | Schlesinger et al. |
| 2011/0319748 A1 | 12/2011 | Bronskill et al. |
| 2012/0029504 A1 | 2/2012 | Afonso et al. |
| 2012/0029511 A1 | 2/2012 | Smith et al. |
| 2012/0029512 A1 | 2/2012 | Willard et al. |
| 2012/0035603 A1 | 2/2012 | Lenihan |
| 2012/0059368 A1 | 3/2012 | Takaoka et al. |
| 2012/0071870 A1 | 3/2012 | Salahieh |
| 2012/0078138 A1 | 3/2012 | Leo et al. |
| 2012/0089123 A1 | 4/2012 | Organ et al. |
| 2012/0101538 A1 | 4/2012 | Ballakur et al. |
| 2012/0116392 A1 | 5/2012 | Willard |
| 2012/0123411 A1 | 5/2012 | Ibrahim et al. |
| 2012/0130364 A1 | 5/2012 | Besch et al. |
| 2012/0136346 A1 | 5/2012 | Condie et al. |
| 2012/0143097 A1 | 6/2012 | Pike, Jr. |
| 2012/0150170 A1 | 6/2012 | Buysse et al. |
| 2012/0157890 A1 | 6/2012 | Govari et al. |
| 2012/0157990 A1 | 6/2012 | Christian |
| 2012/0165809 A1 | 6/2012 | Christian et al. |
| 2012/0172859 A1 | 7/2012 | Condie et al. |
| 2012/0179068 A1 | 7/2012 | Leo et al. |
| 2012/0189998 A1 | 7/2012 | Kruecker et al. |
| 2012/0197243 A1 | 8/2012 | Sherman et al. |

(56) References Cited

U.S. PATENT DOCUMENTS

| | | |
|---|---|---|
| 2012/0239019 A1 | 9/2012 | Asconeguy |
| 2012/0245577 A1 | 9/2012 | Mihalik et al. |
| 2012/0253340 A1 | 10/2012 | Stevenson et al. |
| 2012/0265076 A1 | 10/2012 | Schecter |
| 2012/0265137 A1 | 10/2012 | Mon |
| 2012/0265190 A1 | 10/2012 | Curley et al. |
| 2012/0271306 A1 | 10/2012 | Buysse et al. |
| 2012/0277574 A1 | 11/2012 | Panescu |
| 2012/0277737 A1 | 11/2012 | Curley |
| 2012/0283534 A1 | 11/2012 | Carr et al. |
| 2012/0283722 A1 | 11/2012 | Asconeguy |
| 2012/0302877 A1 | 11/2012 | Harks et al. |
| 2012/0303103 A1 | 11/2012 | Mon et al. |
| 2013/0006139 A1 | 1/2013 | Tiano |
| 2013/0006238 A1 | 1/2013 | Ditter et al. |
| 2013/0030385 A1 | 1/2013 | Schultz et al. |
| 2013/0030426 A1 | 1/2013 | Gallardo et al. |
| 2013/0030427 A1 | 1/2013 | Betts et al. |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079768 A1 | 3/2013 | De Luca et al. |
| 2013/0096447 A1 | 4/2013 | Dhawan et al. |
| 2013/0110104 A1 | 5/2013 | Corvi et al. |
| 2013/0123775 A1 | 5/2013 | Grunewald et al. |
| 2013/0137999 A1 | 5/2013 | Wenzel et al. |
| 2013/0158536 A1 | 6/2013 | Bloom |
| 2013/0172742 A1 | 7/2013 | Rankin et al. |
| 2013/0172873 A1 | 7/2013 | Govari et al. |
| 2013/0172879 A1 | 7/2013 | Sutermeister et al. |
| 2013/0184549 A1 | 7/2013 | Avitall et al. |
| 2013/0190747 A1 | 7/2013 | Koblish et al. |
| 2013/0197504 A1 | 8/2013 | Cronin et al. |
| 2013/0197507 A1 | 8/2013 | Kim et al. |
| 2013/0204124 A1 | 8/2013 | Duindam et al. |
| 2013/0204240 A1 | 8/2013 | McCarthy et al. |
| 2013/0226169 A1 | 8/2013 | Miller et al. |
| 2013/0237977 A1 | 9/2013 | McCarthy et al. |
| 2013/0237979 A1 | 9/2013 | Shikhman et al. |
| 2013/0253504 A1 | 9/2013 | Fang |
| 2013/0253505 A1 | 9/2013 | Schultz |
| 2013/0272339 A1 | 10/2013 | Tofighi |
| 2013/0281851 A1 | 10/2013 | Carr et al. |
| 2013/0289550 A1 | 10/2013 | Ingle et al. |
| 2013/0303892 A1 | 11/2013 | Zhao et al. |
| 2013/0303945 A1 | 11/2013 | Blumenkranz et al. |
| 2013/0310674 A1 | 11/2013 | Deno et al. |
| 2013/0324993 A1 | 12/2013 | McCarthy et al. |
| 2013/0338664 A1 | 12/2013 | Wang et al. |
| 2013/0345692 A1 | 12/2013 | Brannan |
| 2014/0012132 A1 | 1/2014 | Carr et al. |
| 2014/0018697 A1 | 1/2014 | Allison |
| 2014/0018793 A1 | 1/2014 | Sharonov |
| 2014/0025056 A1 | 1/2014 | Dowlatshahi |
| 2014/0025057 A1 | 1/2014 | Hoey et al. |
| 2014/0031785 A1 | 1/2014 | Schwagten et al. |
| 2014/0051959 A1 | 2/2014 | Gliner et al. |
| 2014/0058244 A1 | 2/2014 | Krocak |
| 2014/0058375 A1 | 2/2014 | Koblish |
| 2014/0081111 A1 | 3/2014 | Tun et al. |
| 2014/0081112 A1 | 3/2014 | Kim et al. |
| 2014/0081262 A1 | 3/2014 | Koblish et al. |
| 2014/0094794 A1 | 4/2014 | Orszulak |
| 2014/0142561 A1 | 5/2014 | Reu et al. |
| 2014/0171821 A1 | 6/2014 | Govari et al. |
| 2014/0171936 A1 | 6/2014 | Govari et al. |
| 2014/0180077 A1 | 6/2014 | Huennekens et al. |
| 2014/0187949 A1 | 7/2014 | Zhao et al. |
| 2014/0188440 A1 | 7/2014 | Donhowe et al. |
| 2014/0194867 A1 | 7/2014 | Fish et al. |
| 2014/0207010 A1 | 7/2014 | Schecter |
| 2014/0214017 A1 | 7/2014 | Brannan |
| 2014/0214110 A1 | 7/2014 | Yang et al. |
| 2014/0243813 A1 | 8/2014 | Paul et al. |
| 2014/0249510 A1 | 9/2014 | Koblish et al. |
| 2014/0249521 A1 | 9/2014 | McCarthy et al. |
| 2014/0257261 A1 | 9/2014 | Kim et al. |
| 2014/0276716 A1 | 9/2014 | Melsheimer |
| 2014/0276755 A1 | 9/2014 | Cao et al. |
| 2014/0276811 A1 | 9/2014 | Koblish et al. |
| 2014/0288548 A1 | 9/2014 | Kim et al. |
| 2014/0336638 A1 | 11/2014 | Deem et al. |
| 2014/0343416 A1 | 11/2014 | Panescu et al. |
| 2014/0378956 A1 | 12/2014 | Shafirstein |
| 2015/0011995 A1 | 1/2015 | Avitall et al. |
| 2015/0105645 A1 | 4/2015 | Subramaniam et al. |
| 2015/0126995 A1 | 5/2015 | Govari et al. |
| 2015/0133914 A1 | 5/2015 | Koblish |
| 2015/0133920 A1 | 5/2015 | Rankin et al. |
| 2015/0342676 A1 | 12/2015 | McCarthy et al. |
| 2016/0038229 A1 | 2/2016 | McCarthy et al. |
| 2016/0199131 A1 | 7/2016 | Allison et al. |
| 2016/0278841 A1 | 9/2016 | Panescu et al. |
| 2016/0278842 A1 | 9/2016 | Panescu et al. |
| 2016/0278856 A1 | 9/2016 | Panescu et al. |
| 2016/0317210 A1 | 11/2016 | McCarthy et al. |
| 2016/0324567 A1 | 11/2016 | Panescu et al. |
| 2016/0324568 A1 | 11/2016 | Panescu et al. |

FOREIGN PATENT DOCUMENTS

| | | |
|---|---|---|
| EP | 2008602 | 12/2008 |
| EP | 1803407 | 11/2010 |
| EP | 2294490 | 3/2011 |
| EP | 1962710 | 8/2015 |
| EP | 1962708 | 9/2015 |
| JP | H06-503028 | 4/1994 |
| JP | H06-510450 | 11/1994 |
| JP | T-2002-523127 | 7/2002 |
| JP | 2003-52736 | 2/2003 |
| JP | T-2004-500935 | 1/2004 |
| JP | T-2006-500103 | 1/2006 |
| WO | WO 1993/02747 | 2/1993 |
| WO | WO 1993/04727 | 3/1993 |
| WO | WO 1999/003535 | 1/1999 |
| WO | WO 1999/044523 | 9/1999 |
| WO | WO 2000/010472 | 3/2000 |
| WO | WO 2000/036987 | 6/2000 |
| WO | WO 2001/098764 | 12/2001 |
| WO | WO 2003/028572 | 4/2003 |
| WO | WO 2003/047446 | 6/2003 |
| WO | WO 2003/070298 | 8/2003 |
| WO | WO 2004/026098 | 4/2004 |
| WO | WO 2004/073505 | 9/2004 |
| WO | WO 2004/084748 | 10/2004 |
| WO | WO 2004/107974 | 12/2004 |
| WO | WO 2005/007000 | 1/2005 |
| WO | WO 2006/074571 | 7/2006 |
| WO | WO 2007/019876 | 2/2007 |
| WO | WO 2008/002517 | 1/2008 |
| WO | WO 2010/090701 | 8/2010 |
| WO | WO 2012/120498 | 9/2012 |
| WO | WO 2013/009977 | 1/2013 |
| WO | WO 2013/019544 | 2/2013 |
| WO | WO 2013/034629 | 3/2013 |
| WO | WO 2013/119620 | 8/2013 |
| WO | WO 2013/123020 | 8/2013 |
| WO | WO 2013/138262 | 9/2013 |
| WO | 2013188640 A1 | 12/2013 |
| WO | WO 2014/097300 | 6/2014 |
| WO | WO 2015/033317 | 3/2015 |
| WO | WO 2015/042173 | 3/2015 |
| WO | WO 2015/104672 | 7/2015 |
| WO | WO 2015/200518 | 12/2015 |
| WO | WO 2016/081598 | 5/2016 |
| WO | WO 2016/081602 | 5/2016 |
| WO | WO 2016/081606 | 5/2016 |
| WO | WO 2016/081611 | 5/2016 |
| WO | WO 2016/081650 | 5/2016 |
| WO | 20160153561 | 9/2016 |

(56) References Cited

OTHER PUBLICATIONS

China National Intellectual Property Administration, Notice on the Fourth Office Action and Search Report, for related Chinese Application No. 201580073126.4, dated Dec. 1, 2020, 20 pages.

International Search Report and Written Opinion dated Feb. 3, 2016 for corresponding International Application No. PCT/US2015/061360, International filing date; Nov. 18, 2015; Consisting of 20 pages.

Anter et al, "High-Resolution Mapping of Scar-Related Atrial Arrhythmias Using Smaller Electrodes with Closer Interelectrode Spacing," Circ. Arrhythm. Electrophysiol. 8(3):537-45 (2015).

Arunachalam et al., "Characterization of a digital microwave radiometry system for noninvasive thermometry using temperature controlled homogeneous test load," Phys. Med. Biol. 53(14): 3883-3901, Jul. 21, 2008.

Calkins, "Breaking News! When It Comes to Complications of Catheter Ablation of Atrial Fibrillation, Experience Matters," Circulation, 2013; 128: 2099-2100 (Sep. 2013).

Carr, "Thermography: Radiometric sensing in medicine," New Frontiers in Medical Device Technology, Edited by Rosen et al., pp. 311-342, 1995.

Chierchia et al., "An Initial Clinical Experience with a Novel Microwave Radiometry Sensing Technoiogy used in Irrigated RF Ablatien for Flutter" (date: Jan. 1, 2011).

Constellation™, Full Contact Mapping Catheter, Boston Scientific Corporation Brochure, Dec. 2014.

El-Sharkawy et al., "Absolute temperature monitoring using RF radiometry in the MRI scanner," IEEE Trans Circuits Syst I Regul Pap. 53(11): 2396-2404, Nov. 2006.

Ikeda et al., "Microwave Volumetric Temperature Sensor Improves Control of Radiofrequency Lesion Formation and Steam Pop," Presentation Abstract, May 2012.

Ikeda et al., "Novel Irrigated Radiofrequency Ablation Catheter With Microwave Volumetric Temperature Sensor Predicts Lesion Size and Incidence of Steam Pop in Canine Beating Heart," Presentation Abstract, May 2012.

Jacobsen et al., "Dual-mode antenna design for microwave heating and noninvasive thermometry of superficial tissue disease," IEEE Transactions on Biomedical Engineering 47(11): 1500-1509, Nov. 2000.

Johnson et al., "Automatic Temperature Controller for Multielement Array Hyperthermia Systems", IEEE Transactions on Biomedical Engeineering, vol. 53, No. 6, 1006-1015, Jun. 2016.

Koruth et al., "Occurrence of Steam Pops During Irrigated RF Ablation: Novel Insights from Microwave Radiometry," J. Cardiovasc. Electrophysiol., vol. 24, Issue 11, pp. 1271-1277, Nov. 2013.

Koruth et al., "Tissue Temperature Sensing During Irrigated Radiofrequency Ablation: A Novel Strategy To Predict Steam Pops," Presentation Abstract, May 2012.

Lantis et al, "Microwave Applications in Clinical Medicine," Surgical Endoscopy, vol. 12, Issue 2, pp. 170-176, Feb. 1998.

Panescu et al., Three-Dimensional Finite Element Analysis of Current Density and Temperature Distributions During Radio-Frequency Ablation, IEEE Transactions on Biomedical Engineering (1995) 42(9):879-889.

Price et al., "Novel Ablation Catheter Technology that Improves Mapping Resolution and Monitoring of Lesion Maturation", The Journal of Innovations in Cardiac Rhythm Management, vol. 3, 599-609, Jan. 2012.

Rozen et al., "Prediction of radiofrequency ablation lesion formation using a novel temperature sensing technology incorporated in a force sensing catheter", Heart Rhythm, vol. 14, No. 2, pp. 248-254, Feb. 2017.

Schecter et al., "Palpation of Intra-cardiac Blood Flow, Pressure, Contact Force and Motor Reaction Time of Subjects Using a Novel Haptic Feedback System", Poster Contributions, JACC vol. 65, Issue 10S, Mar. 17, 2015.

Schecter et al., "Tactile Feedback Provides Real Time in Vivo TissuE:Catheter Contact Force Information During Cardiac Radiofrequency Ablation"—Abstract, Journal of Cardiovascular Electrophysiology, vol. 27, No. 5, p. 649, May 2016.

Stevenson, "Irrigated RF ablation: Power titration and fluid management for optimal safety and efficacy," Biosense Webster, Inc., 4 pages, 2005.

Tokmakoff et al., "Thermal Diffusivity Measurements of Natural and Isotopically Enriched Diamond by Picosecond Infrared Transient Grating Experiments," Appl. Phys., A56, pp. 87-90 (1993).

Tungjitkusolmun et al., "Finite element analyses of uniform current density electrodes for radio-frequency cardiac ablation," in IEEE Transactions on Biomedical Engineering, vol. 47, No. 1, pp. 32-40, Jan. 2000.

Tungjitkusolmun et al., "Three-dimensional finite-element analyses for radio-frequency hepatic tumor ablation," in IEEE Transactions on Biomedical Engineering, vol. 49, No. 1, pp. 3-9, Jan. 2002.

Vandekerckhove et al., "Flutter Ablation with an Irrigated Catheter Using Microwave Radiometry Sensing Technology: first report in men" (date: Jan. 1, 2011).

Wang et al., "Microwave Radiometric Thermometry and its Potential Applicability to Ablative Therapy," Journal of Interventional Cardiac Electrophysiology, vol. 4, pp. 295-300, Apr. 2000.

Wang et al., "Tissue Dielectric Measurement Using an Interstitial Dipole Antenna," IEEE Trans Biomed. Eng., vol. 59, No. 1, 115-121, Jan. 2012.

Yazdandoost et al., "Theoretical study of the power distributions for interstitial microwave hyperthermia," Proceedings of the 2002 WSEAS International Conferences, Cadiz, Spain, pp. 1021-1025, Jun. 12-16, 2002.

European Patent Office, Supplementary European Search Report for corresponding Application No. EP 18 79 0093, dated Feb. 15, 2021, 6 pages.

Japan Office Action, dated Apr. 2, 2020 for corresponding JP Application No. 2017-527658, 13 pages.

* cited by examiner

HIGH-RESOLUTION MAPPING OF TISSUE WITH PACING

RELATED APPLICATIONS

This application is a continuation application of U.S. application Ser. No. 15/179,861 filed Jun. 10, 2016, which is a continuation of PCT/US2015/061360, filed Nov. 18, 2015, which claims priority to U.S. Provisional Application No. 62/081,710, filed Nov. 19, 2014, and U.S. Provisional Application No. 62/193,547, filed Jul. 16, 2015, the entire contents of each of which are incorporated herein by reference in their entirety.

BACKGROUND

Tissue ablation may be used to treat a variety of clinical disorders. For example, tissue ablation may be used to treat cardiac arrhythmias by at least partially destroying (e.g., at least partially or completely ablating, interrupting, inhibiting, terminating conduction of, otherwise affecting, etc.) aberrant pathways that would otherwise conduct abnormal electrical signals to the heart muscle. Several ablation techniques have been developed, including cryoablation, microwave ablation, radio frequency (RF) ablation, and high frequency ultrasound ablation. For cardiac applications, such techniques are typically performed by a clinician who introduces a catheter having an ablative tip to the endocardium via the venous vasculature, positions the ablative tip adjacent to what the clinician believes to be an appropriate region of the endocardium based on tactile feedback, mapping electrocardiogram (ECG) signals, anatomy, and/or fluoroscopic imaging, actuates flow of an irrigant to cool the surface of the selected region, and then actuates the ablative tip for a period of time and at a power believed sufficient to destroy tissue in the selected region.

Successful electrophysiology procedures require precise knowledge about the anatomic substrate. Additionally, ablation procedures may be evaluated within a short period of time after their completion. Cardiac ablation catheters typically carry only regular mapping electrodes. Cardiac ablation catheters may incorporate high-resolution mapping electrodes. Such high-resolution mapping electrodes provide more accurate and more detailed information about the anatomic substrate and about the outcome of ablation procedures. High-resolution mapping electrodes can allow the electrophysiology to evaluate precisely the morphology of electrograms, their amplitude and width and to determine changes in pacing thresholds. Morphology, amplitude and pacing threshold are accepted and reliable electrophysiology (EP) markers that provide useful information about the outcome of ablation.

SUMMARY

According to some embodiments, a system for delivering energy to targeted cardiac tissue of a subject and for confirming successful ablation of said targeted cardiac tissue comprises a medical instrument (e.g., catheter) comprising a high-resolution (e.g., split-tip) electrode along a distal end of the catheter, an energy delivery module comprising a processor, the energy delivery module being configured to operatively couple to the catheter, wherein the energy delivery module is configured to energize the electrode to selectively ablate targeted cardiac tissue adjacent the electrode, wherein the energy delivery module is configured to couple to a pacemaker for selectively pacing cardiac tissue in order to attain capture of the heart of the subject, wherein the system is configured, via a predetermined pacing signal provided to the catheter by the pacemaker, to increase the heart rate of the subject from a baseline level to an elevated level, the predetermined pacing signal comprising a pacing level greater than a pre-ablation pacing threshold level, and wherein the processor is configured to terminate the delivery of energy to the electrode after loss of capture of the heart of the subject.

According to some embodiments, wherein the pacemaker is included in the system, the pacemaker is integral to the energy delivery module. In some embodiments, the energy delivery module is configured to deliver radiofrequency (RF) energy to the electrode, wherein the energy delivery module comprises a radiofrequency (RF) generator, wherein the high-resolution electrode comprises a distal portion and a proximal portion, the distal and proximal portions of the high-resolution electrode being operatively coupled to each other using at least one filtering element, wherein the filtering element comprises a capacitor, wherein the pacing level of predetermined pacing signal is 5 to 20 milliamps (mA), wherein the elevated level of the heart rate upon pacing the cardiac tissue at the predetermined pacing level is 100 to 200 beats per minute (bpm), and wherein the energy delivery module comprises at least one filter, the at least one filter being configured to isolate a signal relating to the localized heart rate signal measured using the high-resolution mapping electrode.

According to some embodiments, the pacemaker is included in the system, wherein the high-resolution electrode comprises a distal portion and a proximal portion, the distal and proximal portions of the high-resolution electrode being operatively coupled to each other using at least one filtering element, wherein the filtering element comprises a capacitor, wherein the pacing level of predetermined pacing signal is 5 to 20 milliamps (mA), and wherein the elevated level of the heart rate upon pacing the cardiac tissue at the predetermined pacing level is 100 to 200 beats per minute (bpm).

According to some embodiments, the pacemaker is integral to the energy delivery module. In some embodiments, the pacemaker is separate from the energy delivery module. In some arrangements, the pacemaker is included in the system. In some embodiments, the pacemaker is not included in the system. In some embodiments, the energy delivery module is configured to deliver radiofrequency (RF) energy to the electrode. In some embodiments, the high-resolution electrode comprises a distal portion and a proximal portion, the distal and proximal portions of the high-resolution electrode being operatively coupled to each other using at least one filtering element. In some embodiments, the at least one filtering element comprises a capacitor.

According to some embodiments, the catheter further comprises at least one additional mapping electrode. In some embodiments, the energy delivery module comprises a radiofrequency (RF) generator. In some embodiments, the energy delivery module comprises at least one filter, the at least one filter being configured to isolate a signal relating to the localized heart rate signal measured using the high-resolution mapping electrode. In some embodiments, the pacing level of predetermined pacing signal is 5 to 20 milliamps (mA) (e.g., 5-6, 6-7, 7-8, 8-9, 9-10, 10-11, 11-12, 12-13, 13-14, 14-15, 15-16, 16-17, 17-18, 18-19, 19-20 mA, etc.). In some embodiments, the pacing level of predetermined pacing signal is 10 to 15 milliamps (mA).

According to some embodiments, the elevated level of the heart rate upon pacing the cardiac tissue at the predetermined pacing level is 100 to 200 beats per minute (bpm) (e.g., e.g., 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, 195-200 bpm, etc.). In some embodiments, the elevated level of the heart rate upon pacing the cardiac tissue at the predetermined pacing level is 120 to 150 beats per minute (bpm). In some embodiments, the pre-ablation pacing threshold level is 0.1 to 3 milliamps (mA) (e.g., 0.1-0.2, 0.2-0.3, 0.3-0.4, 0.4-0.5, 0.5-0.6, 0.6-0.7, 0.7-0.8, 0.8-0.9, 0.9-1.0, 1.0-1.1, 1.1-1.2, 1.2-1.3, 1.3-1.4, 1.4-1.5, 1.5-1.6. 1.6-1.7, 1.7-1.8, 1.8-1.9, 1.9-2, 2-2.5, 2.5-3 mA, etc.). In some embodiments, the pre-ablation pacing threshold level is 0.5 to 2 milliamps (mA).

According to some embodiments, the processor is configured to terminate the delivery of energy to the electrode as soon as the heart rate drops below the elevated level or after loss of capture of the heart of the subject. In some embodiments, the processor is configured to terminate the delivery of energy to the electrode following a pre-determined time period after the heart rate drops below the elevated level or after loss of capture of the heart of the subject. In some embodiments, the predetermined time period comprises 0.5 to 10 seconds (e.g., 0.5-1, 1-2, 2-3, 3-4, 4-5, 5-6, 6-7, 7-8, 8-9, 9-10 seconds, values between the foregoing ranges, etc.). In some embodiments, the predetermined time period comprises 1 to 5 seconds.

According to some embodiments, delivery of energy is terminated by an operator with or without a time period after the heart rate drops below the elevated level or after loss of capture of the heart of the subject. In some embodiments, the system further includes at least one output configured to receive data related to the subject's heart rate. In some embodiments, the at least one output comprises a display (e.g., a monitor or other display, etc.). In some embodiments, the at least one output is integrated within the system. In other configurations, the at least one output is separate from the system. In some embodiments, data related to the subject's heart rate are provided via and processed by an EP recording system.

According to some embodiments, a method of ablating and confirming successful ablation of targeted cardiac tissue of a subject using a high-resolution mapping electrode includes pacing said cardiac tissue at a predetermined pacing level to capture the heart of the subject, thereby increasing a heart rate of the subject from a baseline level to an elevated level, delivering ablative energy to the ablation electrode while pacing, the ablation electrode comprising a high-resolution electrode (e.g., a split-tip electrode), wherein the predetermined pacing level exceeds a pre-ablation threshold level, wherein capture of the heart of the subject occurs once the pacing level exceeds the pre-ablation level, and wherein the heart rate of the subject drops below the elevated level when capture of the heart of the subject is lost. The method additionally includes terminating the delivery of ablative energy to the ablation electrode after capture of the heart of the subject is lost.

According to some embodiments, a method of confirming successful ablation of targeted cardiac tissue of a subject using a high-resolution mapping electrode includes pacing said cardiac tissue at a predetermined pacing level to increase a heart rate of the subject from a baseline level to an elevated level, the predetermined pacing level being greater than a pre-ablation pacing threshold level and less than a post-ablation pacing threshold level, delivering ablative energy to the ablation electrode while pacing, the ablation electrode comprising a high-resolution electrode, wherein the heart rate of the subject is at the elevated level once the pre-ablation threshold level is exceeded, but before the post-ablation pacing threshold level is reached, and wherein the heart rate of the subject drops below the elevated level once the ablation electrode has successfully ablated adjacent tissue of the subject, the heart rate has dropped below the elevated level as the post-ablation pacing threshold level is greater than the predetermined pacing level. The method additionally comprises terminating the delivery of ablative energy to the ablation electrode after the heart rate of the subject drops below the elevated level.

According to some embodiments, pacing cardiac tissue is performed via an energy delivery module that is configured to deliver ablative energy to the ablation electrode. In some embodiments, the energy delivery module comprises a radiofrequency (RF) generator. In some embodiments, pacing the cardiac tissue comprises operatively coupling a pacemaker to an energy delivery module that is configured to deliver ablative energy to the ablation electrode. In some embodiments, the pacemaker is integral with the energy delivery module (e.g., RF generator). In some embodiments, the pacemaker is separate from the energy delivery module.

According to some embodiments, the predetermined pacing level is 5 to 20 milliamps (mA) (e.g., 5-6, 6-7, 7-8, 8-9, 9-10, 10-11, 11-12, 12-13, 13-14, 14-15, 15-16, 16-17, 17-18, 18-19, 19-20 mA, etc.). In some embodiments, the pacing threshold is 10 to 15 milliamps (mA). In some embodiments, the elevated level of the heart rate upon pacing the cardiac tissue at the predetermined pacing level is 100 to 200 beats per minute (bpm) (e.g., e.g., 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, 195-200 bpm, etc.). In some embodiments, the elevated level of the heart rate upon pacing the cardiac tissue at the predetermined pacing level is 120 to 150 beats per minute (bpm). In some embodiments, the pre-ablation pacing threshold level is 0.1 to 3 milliamps (mA) (e.g., 0.1-0.2, 0.2-0.3, 0.3-0.4, 0.4-0.5, 0.5-0.6, 0.6-0.7, 0.7-0.8, 0.8-0.9, 0.9-1.0, 1.0-1.1, 1.1-1.2, 1.2-1.3, 1.3-1.4, 1.4-1.5, 1.5-1.6. 1.6-1.7, 1.7-1.8, 1.8-1.9, 1.9-2, 2-2.5, 2.5-3 mA, etc.). In some embodiments, the pre-ablation pacing threshold level is 0.5 to 2 milliamps (mA). In some embodiments, the post-ablation pacing threshold level is greater than 10 milliamps (mA). In some embodiments, the post-ablation pacing threshold level is greater than 20 milliamps (mA).

According to some embodiments, terminating the delivery of ablative energy to the ablation electrode occurs immediately after the heart rate of the subject drops below the elevated level or after capture of the heart of the subject is lost. In some embodiments, terminating the delivery of ablative energy to the ablation electrode occurs following a predetermined time period after the heart rate of the subject drops below the elevated level or after capture of the heart of the subject is lost. In some embodiments, the predetermined time period comprises 0.5 to 10 seconds (e.g., 0.5-1, 1-2, 2-3, 3-4, 4-5, 5-6, 6-7, 7-8, 8-9, 9-10 seconds, values between the foregoing ranges, etc.). In some embodiments, the predetermined time period comprises 1 to 5 seconds. In some embodiments, delivery of energy is terminated by an operator with or without a time period after the heart rate drops below the elevated level or after loss of capture of the heart of the subject.

According to some embodiments, the method additional includes providing data related to the heart rate of the subject to at least one output. In some embodiments, the at least one output comprises a display (e.g., display, other monitor, etc.). In some embodiments, data related to the heart rate of the subject are provided via and processed by an electrophysiology (EP) recording system. In some embodiments, delivering ablative energy to the ablation electrode comprises delivering radiofrequency (RF) energy.

According to some embodiments, a system for delivering energy to targeted cardiac tissue of a subject and for confirming successful ablation of said targeted cardiac tissue comprises a catheter comprising a high-resolution electrode along a distal end of the catheter, an energy delivery module (e.g., generator) comprising a processor, the energy delivery module being configured to operatively couple to the catheter, wherein the energy delivery module is configured to energize the electrode to selectively ablate targeted cardiac tissue adjacent the electrode, wherein the energy delivery module is configured to couple to a pacemaker for selectively pacing cardiac tissue in order to selectively increase a heart rate of the subject, wherein the system is configured, via a predetermined pacing signal provided to the catheter by the pacemaker, to increase the heart rate of the subject from a baseline level to an elevated level, the predetermined pacing signal comprising a pacing level greater than a pre-ablation pacing threshold level and less than a post-ablation pacing threshold level, wherein a heart rate of the subject is at the elevated level before the post-ablation pacing threshold level is achieved, wherein a heart rate of the subject falls below the elevated level once the high-resolution electrode has ablated adjacent tissue to a target therapeutic level, and wherein the processor is configured to terminate the delivery of energy to the electrode after the subject's heart rate drops below the elevated level.

According to some embodiments, the pacemaker is integral to the energy delivery module. In some embodiments, the pacemaker is separate from the energy delivery module. In some embodiments, the pacemaker is included in the system. In some configurations, the pacemaker is not included in the system.

According to some embodiments, the energy delivery module is configured to deliver radiofrequency (RF) energy to the electrode. In some embodiments, the electrode comprises a high-resolution electrode having a distal portion and a proximal portion, the distal and proximal portions of the high-resolution electrode being operatively coupled to each other using at least one filtering element. In some embodiments, the at least one filtering element comprises a capacitor.

According to some embodiments, the catheter further comprises at least one additional mapping electrode. In some embodiments, the energy delivery module comprises a radiofrequency (RF) generator. In some embodiments, the energy delivery module comprises at least one filter, the at least one filter being configured to isolate a signal relating to the localized heart rate signal measured using the high-resolution mapping electrode.

According to some embodiments, the predetermined pacing level is 5 to 20 milliamps (mA) (e.g., 5-6, 6-7, 7-8, 8-9, 9-10, 10-11, 11-12, 12-13, 13-14, 14-15, 15-16, 16-17, 17-18, 18-19, 19-20 mA, etc.). In some embodiments, the pacing threshold is 10 to 15 milliamps (mA). In some embodiments, the elevated level of the heart rate upon pacing the cardiac tissue at the predetermined pacing level is 100 to 200 beats per minute (bpm) (e.g., e.g., 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, 195-200 bpm, etc.). In some embodiments, the elevated level of the heart rate upon pacing the cardiac tissue at the predetermined pacing level is 120 to 150 beats per minute (bpm). In some embodiments, the pre-ablation pacing threshold level is 0.1 to 3 milliamps (mA) (e.g., 0.1-0.2, 0.2-0.3, 0.3-0.4, 0.4-0.5, 0.5-0.6, 0.6-0.7, 0.7-0.8, 0.8-0.9, 0.9-1.0, 1.0-1.1, 1.1-1.2, 1.2-1.3, 1.3-1.4, 1.4-1.5, 1.5-1.6, 1.6-1.7, 1.7-1.8, 1.8-1.9, 1.9-2, 2-2.5, 2.5-3 mA, etc.). In some embodiments, the pre-ablation pacing threshold level is 0.5 to 2 milliamps (mA). In some embodiments, the post-ablation pacing threshold level is greater than 10 milliamps (mA). In some embodiments, the post-ablation pacing threshold level is greater than 20 milliamps (mA).

According to some embodiments, the processor is configured to terminate the delivery of energy to the electrode as soon as the heart rate drops below the elevated level or after loss of capture of the heart of the subject. In some embodiments, the processor is configured to terminate the delivery of energy to the electrode following a pre-determined time period after the heart rate drops below the elevated level or after loss of capture of the heart of the subject. In some embodiments, the predetermined time period comprises 0.5 to 10 seconds (e.g., 0.5-1, 1-2, 2-3, 3-4, 4-5, 5-6, 6-7, 7-8, 8-9, 9-10 seconds, values between the foregoing ranges, etc.). In some embodiments, the predetermined time period comprises 1 to 5 seconds.

According to some embodiments, the system is configured so that delivery of energy is terminated by an operator with or without a time period after the heart rate drops below the elevated level or after loss of capture of the heart of the subject. In some embodiments, the system further comprises at least one output configured to receive data related to the subject's heart rate. In some embodiments, the at least one output comprises a display (e.g., monitor, other display, etc.). In some embodiments, the at least one output is integrated within the system. In other configurations, the at least one output is separate from the system.

According to some embodiments, data related to the subject's heart rate are provided via and processed by an EP recording system. In some embodiments, the post-ablation pacing threshold level is greater than 10 milliamps (mA). In some arrangements, the post-ablation pacing threshold level is greater than 20 milliamps (mA).

According to some embodiments, an energy delivery module (e.g., a generator) configured to deliver ablative energy to targeted cardiac tissue of a subject and for confirming successful ablation of said targeted cardiac tissue includes a processor for regulating the delivery of ablative energy, wherein the energy delivery module is configured to operatively couple to a catheter, wherein the energy delivery module is configured to energize an electrode positioned along a distal end of the catheter to selectively ablate targeted cardiac tissue adjacent the electrode, wherein the energy delivery module is configured to couple to a pacemaker for selectively pacing cardiac tissue in order to attain capture of the heart of the subject, wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level, and wherein the processor is configured to terminate the delivery of energy to the electrode after loss of capture of the heart of the subject.

According to some embodiments, the energy delivery module further comprises a pacemaker. In some embodiments, the pacemaker is integrated within the module. In some embodiments, the pacemaker is separate from the module.

According to some embodiments, a kit for delivering ablative energy to targeted cardiac tissue of a subject and for confirming successful ablation of said targeted cardiac tissue comprises a catheter including a high-resolution electrode (e.g., a split-tip electrode) along a distal end of the catheter, and an energy delivery module comprising a processor, wherein the processor is configured to regulate the delivery of ablative energy, wherein the energy delivery module is configured to operatively couple to the catheter, wherein the energy delivery module is configured to energize the electrode positioned along a distal end of the catheter to selectively ablate targeted cardiac tissue adjacent the electrode, wherein the energy delivery module is configured to couple to a pacemaker for selectively pacing cardiac tissue in order to attain capture of the heart of the subject, wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level, and wherein the processor is configured to terminate the delivery of energy to the electrode after loss of capture of the heart of the subject.

According to some embodiments, the kit further comprises the pacemaker. In some embodiments, the pacemaker is integrated within the energy delivery module. In other configurations, the pacemaker is separate from the energy delivery module. In one embodiment, the energy delivery module is configured to receive (e.g., via a port, coupling, other wired connection, a wireless connection, etc.) a pacemaker.

According to some embodiments, a processor configured for use with an energy delivery module configured to deliver ablative energy to targeted cardiac tissue of a subject and for confirming successful ablation of said targeted cardiac tissue is configured to regulate the delivery of ablative energy from an energy delivery module to an electrode, wherein the energy delivery module is configured to operatively couple to a catheter comprising the electrode, wherein the energy delivery module is configured to energize the electrode positioned along a distal end of the catheter to selectively ablate targeted cardiac tissue adjacent the electrode, wherein the processor is configured to couple to a pacemaker for selectively pacing cardiac tissue in order to attain capture of the heart of the subject, wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level, and wherein the processor is configured to terminate the delivery of energy to the electrode after loss of capture of the heart of the subject. According to some embodiments, the processor is directly or indirectly coupled to a pacemaker.

According to some embodiments, a generator configured to deliver ablative energy to targeted cardiac tissue of a subject and for confirming successful ablation of said targeted cardiac tissue comprises an energy delivery module configured to generate ablative energy for delivery to an ablation device, and a processor configured to regulate the delivery of ablative energy from the energy delivery module to an electrode of the ablation device, wherein ablative energy generated by the energy delivery module is delivered to the electrode assembly, wherein the energy delivery module is configured to couple to a pacemaker for selectively pacing cardiac tissue in order to attain capture of the heart of the subject, wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level, and wherein the processor is configured to terminate the delivery of energy to the electrode after loss of capture of the heart of the subject.

According to some embodiments, the energy delivery module is configured to generated radiofrequency (RF) energy. In some embodiments, the processor and the energy delivery module are located within a single housing or enclosure. In some embodiments, the processor and the energy delivery module are located within separate housings or enclosures. In some embodiments, the generator includes the pacemaker. In some embodiments, the pacemaker is integral to the energy delivery module. In other arrangements, the pacemaker is separate from the energy delivery module.

According to some embodiments, the electrode comprises a high-resolution electrode (e.g., split-tip electrode). In some embodiments, the high resolution electrode comprises a distal portion and a proximal portion, the distal and proximal portions of the high-resolution electrode being operatively coupled to each other using at least one filtering element. In some embodiments, the at least one filtering element comprises a capacitor.

BRIEF DESCRIPTION OF THE DRAWINGS

These and other features, aspects and advantages of the present application are described with reference to drawings of certain embodiments, which are intended to illustrate, but not to limit, the concepts disclosed herein. The attached drawings are provided for the purpose of illustrating concepts of at least some of the embodiments disclosed herein and may not be to scale.

DETAILED DESCRIPTION

According to some embodiments, successful electrophysiology procedures require precise knowledge about the anatomic substrate being targeted. Additionally, it may be desirable to evaluate the outcome of an ablation procedure within a short period of time after the execution of the procedure (e.g., to confirm that the desired clinical outcome was achieved). Typically, ablation catheters include only regular mapping electrodes (e.g., ECG electrodes). However, in some embodiments, it may be desirable for such catheters to incorporate high-resolution mapping capabilities. In some embodiments, high-resolution mapping electrodes can provide more accurate and more detailed information about the anatomic substrate and about the outcome of ablation procedures. For example, such high-resolution mapping electrodes can allow the electrophysiology (EP) practitioner to evaluate the morphology of electrograms, their amplitude and width and/or to determine changes in pacing thresholds. According to some arrangements, morphology, amplitude and/or pacing threshold are accepted as reliable EP markers that provide useful information about the outcome of ablation. Thus, high-resolution electrodes are defined as any electrode(s) capable of delivering ablative or other energy to tissue capable of transferring heat to/from such tissue, while being capable of obtaining accurate mapping data of adjacent tissue, and include, without limitation, split-tip RF electrodes, other closely oriented electrodes or electrode portions and/or the like.

Several embodiments disclosed herein are particularly advantageous because they include one, several or all of the following benefits or advantages: reducing proximal edge heating, reducing the likelihood of char formation, providing for feedback that may be used to adjust ablation procedures in real time, providing noninvasive temperature measurements, providing safer and more reliable ablation procedures, providing for confirmation that a targeted region of tissue being treated has been properly ablated (e.g., using confirmation related to capture of the heart) and/or the like.

According to some embodiments, various implementations of electrodes (e.g., radiofrequency or RF electrodes) that can be used for high-resolution mapping are disclosed herein. For example, as discussed in greater detail herein, an ablation or other energy delivery system can comprise a high-resolution-tip design, wherein the energy delivery member (e.g., radiofrequency electrode) comprises two or more separate electrodes or electrode portions. As also discussed herein, in some embodiments, such separate electrodes or electrode portions can be advantageously electrically coupled to each other (e.g., to collectively create the desired heating or ablation of targeted tissue).

Figure 1:
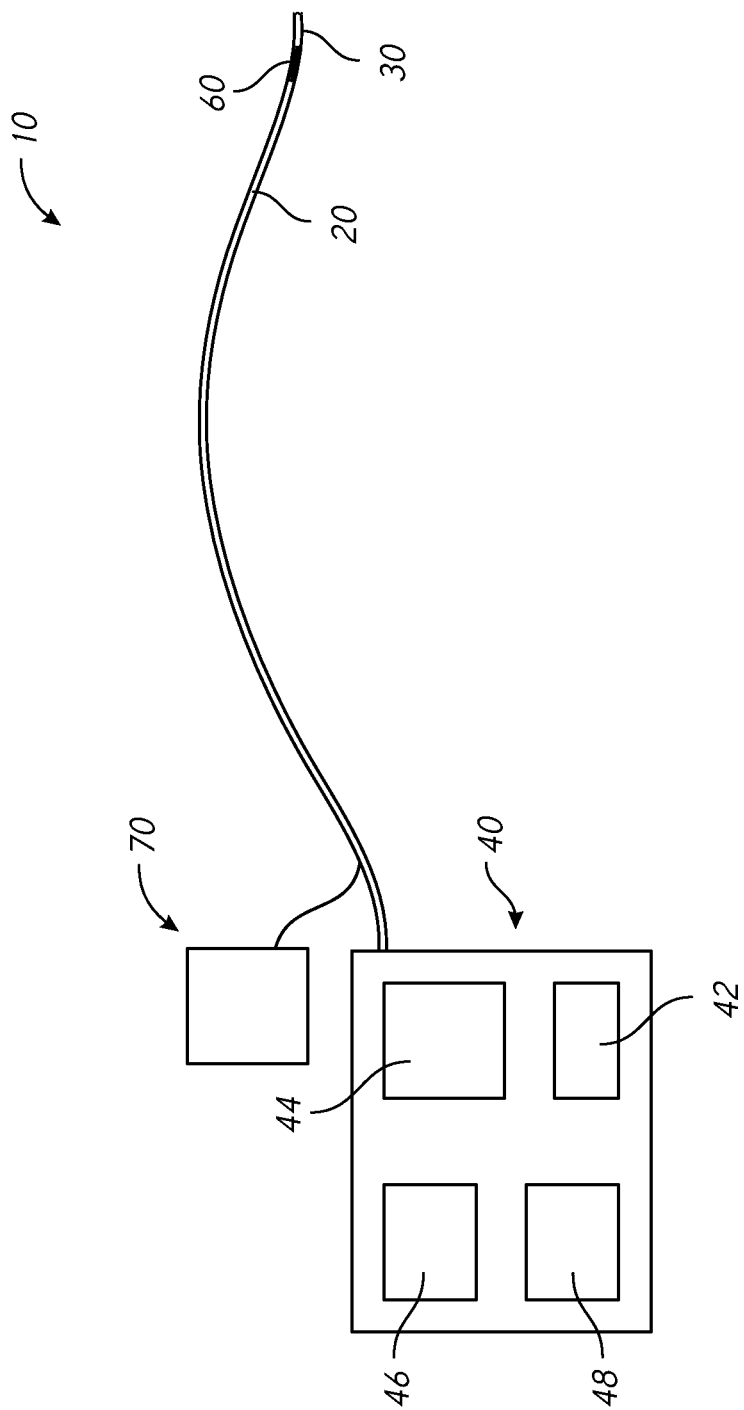
FIG. 1 schematically illustrates one embodiment of an energy delivery system configured to selectively ablate or otherwise heat targeted tissue of a subject.

FIG. 1 schematically illustrates one embodiment of an energy delivery system 10 that is configured to selectively ablate, stimulate, modulate and/or otherwise heat or treat targeted tissue (e.g., cardiac tissue, pulmonary vein, other vessels or organs, etc.). Although certain embodiments disclosed herein are described with reference to ablation systems and methods, any of the systems and methods can be used to stimulate, modulate, heat and/or otherwise affect tissue, with or without partial or complete ablation, as desired or required. As shown, the system 10 can include a medical instrument 20 (e.g., catheter) comprising one or more energy delivery members 30 (e.g., radiofrequency electrodes) along a distal end of the medical instrument 20. The medical instrument can be sized, shaped and/or otherwise configured to be passed intraluminally (e.g., intravascularly) through a subject being treated. In various embodiments, the medical instrument 20 comprises a catheter, a shaft, a wire, and/or other elongate instrument. In other embodiments, the medical instrument is not positioned intravascularly but is positioned extravascularly via laparoscopic or open surgical procedures. In various embodiments, the medical instrument 20 comprises a catheter, a shaft, a wire, and/or other elongate instrument. In some embodiments, one or more temperature sensing devices or systems 60 (e.g., thermocouples, thermistors, etc.) may be included at the distal end of the medical instrument 20, or along its elongate shaft or in its handle. The term "distal end" does not necessarily mean the distal terminus or distal end. Distal end could mean the distal terminus or a location spaced from the distal terminus but generally at a distal end portion of the medical instrument 20.

In some embodiments, the medical instrument 20 is operatively coupled to one or more devices or components. For example, as depicted in FIG. 1, the medical instrument 20 can be coupled to a delivery module 40 (such as an energy delivery module). According to some arrangements, the energy delivery module 40 includes an energy generation device 42 that is configured to selectively energize and/or otherwise activate the energy delivery member(s) 30 (for example, radiofrequency electrodes) located along the medical instrument 20. In some embodiments, for instance, the energy generation device 42 comprises a radiofrequency generator, an ultrasound energy source, a microwave energy source, a laser/light source, another type of energy source or generator, and the like, and combinations thereof. In other embodiments, energy generation device 42 is substituted with or use in addition to a source of fluid, such a cryogenic fluid or other fluid that modulates temperature. Likewise, the delivery module (e.g., delivery module 40), as used herein, can also be a cryogenic device or other device that is configured for thermal modulation.

With continued reference to the schematic of FIG. 1, the energy delivery module 40 can include one or more input/output devices or components 44, such as, for example, a touchscreen device, a screen or other display, a controller (e.g., button, knob, switch, dial, etc.), keypad, mouse, joystick, trackpad, or other input device and/or the like. Such devices can permit a physician or other user to enter information into and/or receive information from the system 10. In some embodiments, the output device 44 can include a touchscreen or other display that provides tissue temperature information, contact information, other measurement information and/or other data or indicators that can be useful for regulating a particular treatment procedure.

According to some embodiments, the energy delivery module 40 includes a processor 46 (e.g., a processing or control unit) that is configured to regulate one or more aspects of the treatment system 10. The module 40 can also comprise a memory unit or other storage device 48 (e.g., computer readable medium) that can be used to store operational parameters and/or other data related to the operation of the system 10. In some embodiments, the processor 46 is configured to automatically regulate the delivery of energy from the energy generation device 42 to the energy delivery member 30 of the medical instrument 20 based on one or more operational schemes. For example, energy provided to the energy delivery member 30 (and thus, the amount of heat transferred to or from the targeted tissue) can be regulated based on, among other things, the detected temperature of the tissue being treated.

According to some embodiments, the energy delivery system 10 can include one or more temperature detection devices, such as, for example, reference temperature devices (e.g., thermocouples, thermistors, etc.) and/or the like. For example, in some embodiments, the device further comprises a one or more temperature sensors or other temperature-measuring devices to help determine a peak (e.g., high or peak, low or trough, etc.) temperature of tissue being treated. In some embodiments, the temperature sensors (e.g., thermocouples) located at, along and/or near the ablation member (e.g., RF electrode) can help with the determination of whether contact is being made between the ablation member and targeted tissue (and/or to what degree such contact is being made). In some embodiments, such peak temperature is determined without the use of radiometry.

With reference to FIG. 1, the energy delivery system 10 comprises (or is in configured to be placed in fluid communication with) an irrigation fluid system 70. In some embodiments, as schematically illustrated in FIG. 1, such a fluid system 70 is at least partially separate from the energy delivery module 40 and/or other components of the system 10. However, in other embodiments, the irrigation fluid system 70 is incorporated, at least partially, into the energy delivery module 40. The irrigation fluid system 70 can include one or more pumps or other fluid transfer devices that are configured to selectively move fluid through one or more lumens or other passages of the catheter 20. Such fluid can be used to selectively cool (e.g., transfer heat away from) the energy delivery member 30 during use.

Figure 2:
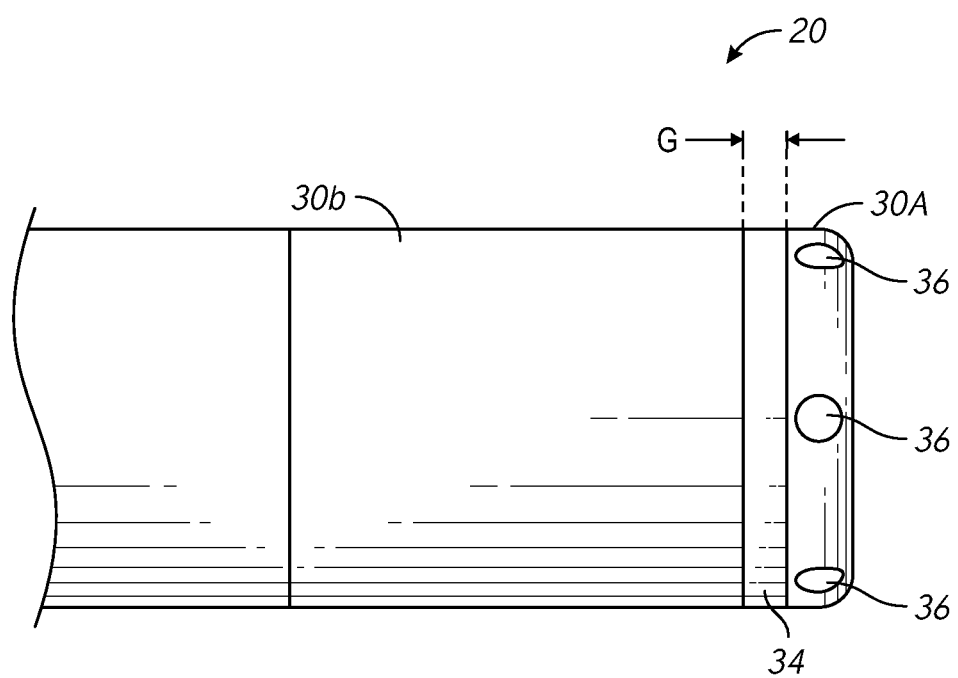
FIG. 2 illustrates a side view of a system's catheter comprises a high-resolution-tip design according to one embodiment.

FIG. 2 illustrates one embodiment of a distal end of a medical instrument (e.g., catheter) 20. As shown, the catheter 20 can include a high-resolution tip design, such that there are two adjacent electrodes or two adjacent electrode portions 30A, 30B separated by a gap G. According to some embodiments, as depicted in the configuration of FIG. 2, the relative length of the different electrodes or electrode portions 30A, 30B can vary. For example, the length of the proximal electrode 30B can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 30A, as desired or required. In other embodiments, the length of the proximal electrode 30B can be greater than 20 times (e.g., 20-25, 25-30, more than 30 times, etc.) the length of the distal electrode 30A. In yet other embodiments, the lengths of the distal and proximal electrodes 30A, 30B are about equal. In some embodiments, the distal electrode 30A is longer than the proximal electrode 30B (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

In some embodiments, the distal electrode or electrode portion 30A is 0.5 mm long. In other embodiments, the distal electrode or electrode portion 30A is between 0.1 mm and 1 mm long (e.g., 0.1-0.2, 0.2-0.3, 0.3-0.4, 0.4-0.5, 0.5-0.6, 0.6-0.7, 0-0.8, 0.8-0.9, 0.9-1 mm, values between the foregoing ranges, etc.). In other embodiments, the distal electrode or electrode portion 30A is greater than 1 mm in length, as desired or required. In some embodiments, the proximal electrode or electrode portion 30B is 2 to 4 mm long (e.g., 2-2.5, 2.5-3, 3-3.5, 3.5-4 mm, lengths between the foregoing, etc.). However, in other embodiments, the proximal electrode portion 30B is greater than 4 mm (e.g., 4-5, 5-6, 6-7, 7-8, 8-9, 9-10 mm, greater than 10 mm, etc.) or smaller than 1 mm (e.g., 0.1-0.5 0.5-1, 1-1.5, 1.5-2 mm, lengths between the foregoing ranges, etc.), as desired or required. In embodiments where the high-resolution electrodes are located on catheter shafts, the length of the electrodes can be 1 to 5 mm (e.g., 1-2, 2-3, 3-4, 4-5 mm, lengths between the foregoing, etc.). However, in other embodiments, the electrodes can be longer than 5 mm (e.g., 5-6, 6-7, 7-8, 8-9, 9-10, 10-15, 15-20 mm, lengths between the foregoing, lengths greater than 20 mm, etc.), as desired or required.

As noted above, the use of a high-resolution tip design can permit a user to simultaneously ablate or otherwise thermally treat targeted tissue and map (e.g., using high-resolution mapping) in a single configuration. Thus, such systems can advantageously permit precise high-resolution mapping (e.g., to confirm that a desired level of treatment occurred) during a procedure. In some embodiments, the high-resolution tip design that includes two electrodes or electrode portions 30A, 30B can be used to record a high-resolution bipolar electrogram. For such purposes, the two electrodes or electrode portions can be connected to the inputs of an EP recorder. In some embodiments, a relatively small separation distance (e.g., gap G) between the electrodes or electrode portions 30A, 30B enables high-resolution mapping.

In some embodiments, a medical instrument (e.g., a catheter) 20 can include three or more electrodes or electrode portions (e.g., separated by gaps), as desired or required. Additional details regarding such arrangements are provided below. According to some embodiments, regardless of how many electrodes or electrode portions are positioned along a catheter tip, the electrodes or electrode portions 30A, 30B are radiofrequency electrodes and comprise one or more metals, such as, for example, stainless steel, platinum, platinum-iridium, gold, gold-plated alloys and/or the like.

According to some embodiments, as illustrated in FIG. 2, the electrodes or electrode portions 30A, 30B are spaced apart from each other (e.g., longitudinally or axially) using a gap (e.g., an electrically insulating gap). In some embodiments, the length of the gap G (or the separation distance between adjacent electrodes or electrode portions) is 0.5 mm. In other embodiments, the gap G or separation distance is greater or smaller than 0.5 mm, such as, for example, 0.1-1 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, a separator 34 is positioned within the gap G, between the adjacent electrodes or electrode portions 30A, 30B, as depicted in FIG. 2. The separator can comprise one or more electrically insulating materials, such as, for example, Teflon, polyetheretherketone (PEEK), polyetherimide resins (e.g., ULTEM™), ceramic materials, polyimide and the like.

As noted above with respect to the gap G separating the adjacent electrodes or electrode portions, the insulating separator 34 can be 0.5 mm long. In other embodiments, the length of the separator 34 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, as discussed in greater detail herein, to ablate or otherwise heat or treat targeted tissue of a subject successfully with the high-resolution tip electrode design, such as the one depicted in FIG. 2, the two electrodes or electrode portions 30A, 30B are electrically coupled to each other at the RF frequency. Thus, the two electrodes or electrode portions can advantageously function as a single longer electrode at the RF frequency.

Figure 3:
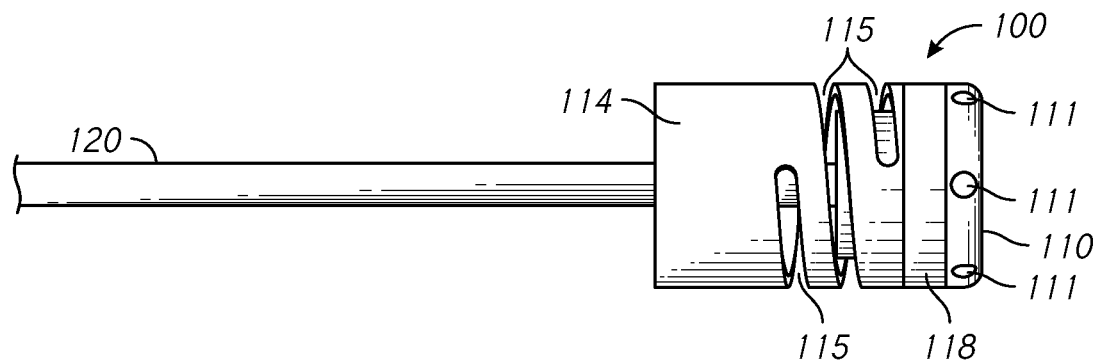
FIG. 3 illustrates a side view of a system's catheter comprises a high-resolution-tip design according to another embodiment.
Figure 4:
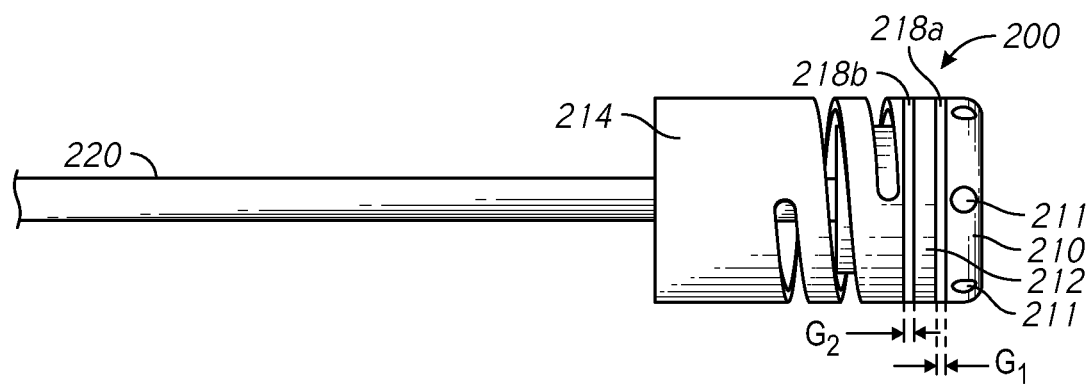
FIG. 4 illustrates a side view of a system's catheter comprises a high-resolution-tip design according to yet another embodiment.

FIGS. 3 and 4 illustrate different embodiments of catheter systems 100, 200 that incorporate a high-resolution tip design. For example, in FIG. 3, the electrode (e.g., radiofrequency electrode) along the distal end of the electrode comprises a first or distal electrode or electrode portion 110 and a second or proximal electrode or electrode portion 114. As shown and discussed in greater detail herein with reference to other configurations, the high-resolution tip design 100 includes a gap G between the first and second electrodes or electrode portions 110, 114. In some configurations, the second or proximal electrode or electrode portion 114 is generally longer than the first or distal electrode or electrode portion 110. For instance, the length of the proximal electrode 114 can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 110, as desired or required. In other embodiments, the length of the proximal electrode can be greater than 20 times (e.g., 20-25, 25-30, more than 30 times, etc.) the length of the distal electrode. In yet other embodiments, the lengths of the distal and proximal electrodes are about the same. However, in some embodiments, the distal electrode 110 is longer than the proximal electrode 114 (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

As shown in FIG. 3 and noted above, regardless of their exact design, relative length diameter, orientation and/or other characteristics, the electrodes or electrode portions 110, 114 can be separated by a gap G. The gap G can comprise a relatively small electrically insulating gap or space. In some embodiments, an electrically insulating separator 118 can be snugly positioned between the first and second electrodes or electrode portions 110, 114. In certain embodiments, the separator 118 can have a length of about 0.5 mm. In other embodiments, however, the length of the separator 118 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required. The separator can include one or more electrically insulating materials (e.g., materials that have an electrical conductivity less than about 1000 or less (e.g., 500-600, 600-700, 700-800, 800-900, 900-1000, 1000-1100, 1100-1200, 1200-1300, 1300-1400, 1400-1500, values between the foregoing, less than 500, greater than 1500, etc.) than the electrical conductivity of metals or alloys). The separator can comprise one or more electrically insulating materials, such as, for example, Teflon, polyetheretherketone (PEEK), polyoxymethylene, acetal resins or polymers and the like.

As shown in FIG. 3, the separator 118 can be cylindrical in shape and can have the identical or similar diameter and configuration as the adjacent electrodes or electrode portions 110, 114. Thus, in some embodiments, the outer surface formed by the electrodes or electrode portions 110, 114 and the separator 118 can be generally uniform or smooth. However, in other embodiments, the shape, size (e.g., diameter) and/or other characteristics of the separator 118 can be different than one or more of the adjacent electrodes or electrode portions 110, 114, as desired or required for a particular application or use.

FIG. 4 illustrates an embodiment of a system 200 having three or more electrodes or electrode portions 210, 212, 214 separated by corresponding gaps G1, G2. The use of such additional gaps, and thus, additional electrodes or electrode portions 210, 212, 214 that are physically separated (e.g., by gaps) yet in close proximity to each other, can provide additional benefits to the high-resolution mapping capabilities of the system. For example, the use of two (or more) gaps can provide more accurate high-resolution mapping data related to the tissue being treated. Such multiple gaps can provide information about the directionality of cardiac signal propagation. In addition, high-resolution mapping with high-resolution electrode portions involving multiple gaps can provide a more extended view of lesion progression during the ablation process and higher confidence that viable tissue strands are not left behind within the targeted therapeutic volume. In some embodiments, high-resolution electrodes with multiple gaps can optimize the ratio of mapped tissue surface to ablated tissue surface. Preferably, such ratio is in the range of 0.2 to 0.8 (e.g., 0.2-0.3, 0.3-0.4, 0.4-0.5, 0.5-0.6, 0.6-0.7, 0.7-0.8, ratios between the foregoing, etc.). Although FIG. 4 illustrates an embodiment having a total of three electrodes or electrode portions 210, 212, 214 (and thus, two gaps G1, G2), a system can be designed or otherwise modified to comprise additional electrodes or electrode portions, and thus, additional gaps. For example, in some embodiments, an ablation or other treatment system can include 4 or more (e.g., 5, 6, 7, 8, more than 8, etc.) electrodes or electrode portions (and thus, 3 or more gaps, e.g., 3, 4, 5, 6, 7 gaps, more than 7 gaps, etc.), as desired or required. In such configurations, a gap (and/or an electrical separator) can be positioned between adjacent electrodes or electrode portions, in accordance with the embodiments illustrated in FIGS. 2 to 4.

As depicted in FIGS. 3 and 4, an irrigation tube 120, 220 can be routed within an interior of the catheter (not shown for clarity). In some embodiments, the irrigation tube 120, 220 can extend from a proximal portion of the catheter (e.g., where it can be placed in fluid communication with a fluid pump) to the distal end of the system. For example, in some arrangements, as illustrated in the side views of FIGS. 3 and 4, the irrigation tube 120, 220 extends and is in fluid communication with one or more fluid ports 211 that extend radially outwardly through the distal electrode 110, 210. Thus, in some embodiments, the treatment system comprises an open irrigation design, wherein saline and/or other fluid is selectively delivered through the catheter (e.g., within the fluid tube 120, 220) and radially outwardly through one or more outlet ports 111, 211 of an electrode 110, 210. The delivery of such saline or other fluid can help remove heat away from the electrodes and/or the tissue being treated. In some embodiments, such an open irrigation system can help prevent or reduce the likelihood of overheating of targeted tissue, especially along the tissue that is contacted by the electrodes. An open irrigation design is also incorporated in the system that is schematically illustrated in FIG. 2. For instance, as depicted in FIG. 2, the distal electrode or electrode portion 34 can include a plurality of outlet ports 36 through which saline or other irrigation fluid can exit.

Figure 5:
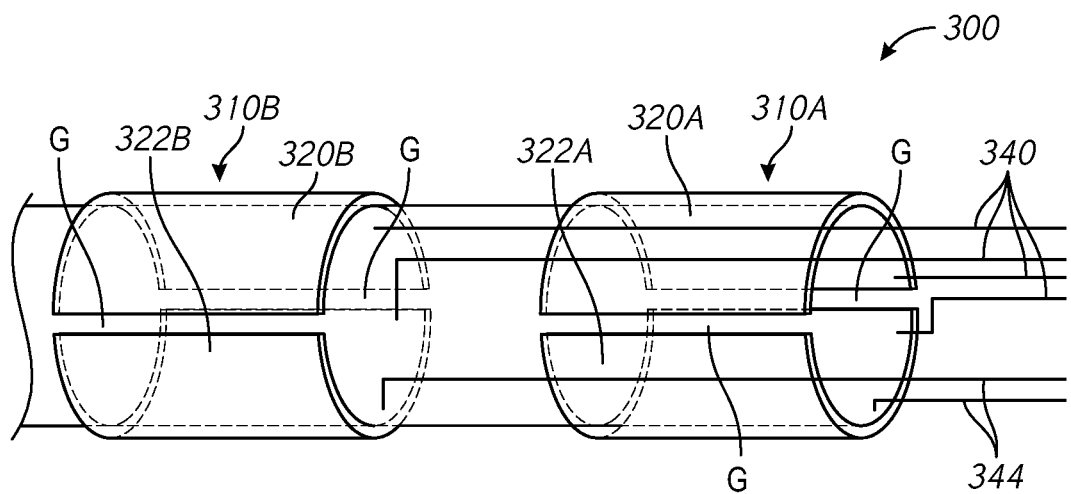
FIG. 5 illustrates an embodiment of a system's catheter comprising two high-resolution-section electrodes each consisting of separate sections circumferentially distributed on the catheter shaft.

According to some embodiments, a catheter can include a high-resolution-tip electrode design that includes one or more gaps in the circumferential direction (e.g., radially), either in addition to or in lieu of gaps in the longitudinal direction. One embodiment of a system 300 comprising one or more electrodes 310A, 310B is illustrated in FIG. 5. As shown, in arrangements where two or more electrodes are included, the electrodes 310A, 310B can be longitudinally or axially offset from each other. For example, in some embodiments, the electrodes 310A, 310B are located along or near the distal end of a catheter. In some embodiments, the electrodes 310A, 310B are located along an exterior portion of a catheter or other medical instrument. However, in other configurations, one or more of the electrodes can be positioned along a different portion of the catheter or other medical instrument (e.g., along at least an interior portion of a catheter), as desired or required.

With continued reference to FIG. 5, each electrode 310A, 310B can comprises two or more sections 320A, 322A and/or 320B, 320B. As shown, in some embodiments, the each section 320A, 322A and/or 320B, 320B can extend half-way around (e.g., 180 degrees) the diameter of the catheter. However, in other embodiments, the circumferential extent of each section can be less than 180 degrees. For example, each section can extend between 0 and 180 degrees (e.g., 15, 30, 45, 60, 75, 90, 105, 120 degrees, degrees between the foregoing, etc.) around the circumference of the catheter along which it is mounted. Thus, in some embodiments, an electrode can include 2, 3, 4, 5, 6 or more circumferential sections, as desired or required.

Regardless of how the circumferential electrode sections are designed and oriented, electrically insulating gaps G can be provided between adjacent sections to facilitate the ability to use the electrode to conduct high-resolution mapping, in accordance with the various embodiments disclosed herein. Further, as illustrated in the embodiment of FIG. 5, two or more (e.g., 3, 4, 5, more than 5, etc.) electrodes 310A, 310B having two or more circumferential or radial sections can be included in a particular system 300, as desired or required.

In alternative embodiments, the various embodiments of a high-resolution tip design disclosed herein, or variations thereof, can be used with a non-irrigated system or a closed-irrigation system (e.g., one in which saline and/or other fluid is circulated through or within one or more electrodes to selectively remove heat therefrom). Thus, in some arrangements, a catheter can include two or more irrigation tubes or conduits. For example, one tube or other conduit can be used to deliver fluid toward or near the electrodes, while a second tube or other conduit can be used to return the fluid in the reverse direction through the catheter.

According to some embodiments, a high-resolution tip electrode is designed to balance the current load between the various electrodes or electrode portions. For example, if a treatment system is not carefully configured, the electrical load may be delivered predominantly to one or more of the electrodes or electrode portions of the high-resolution tip system (e.g., the shorter or smaller distal electrode or electrode portion). This can lead to undesirable uneven heating of the electrode, and thus, uneven heating (e.g., ablation) of the adjacent tissue of the subject. Thus, in some embodiments, one or more load balancing configurations can be used to help ensure that the heating along the various electrodes or electrode portions of the system will be generally balanced. As a result, the high-resolution tip design can advantageously function more like a longer, single electrode, as opposed to two or more electrodes that receive an unequal electrical load (and thus, deliver an unequal amount of heat or level of treatment to the subject's targeted tissue).

Figure 6:
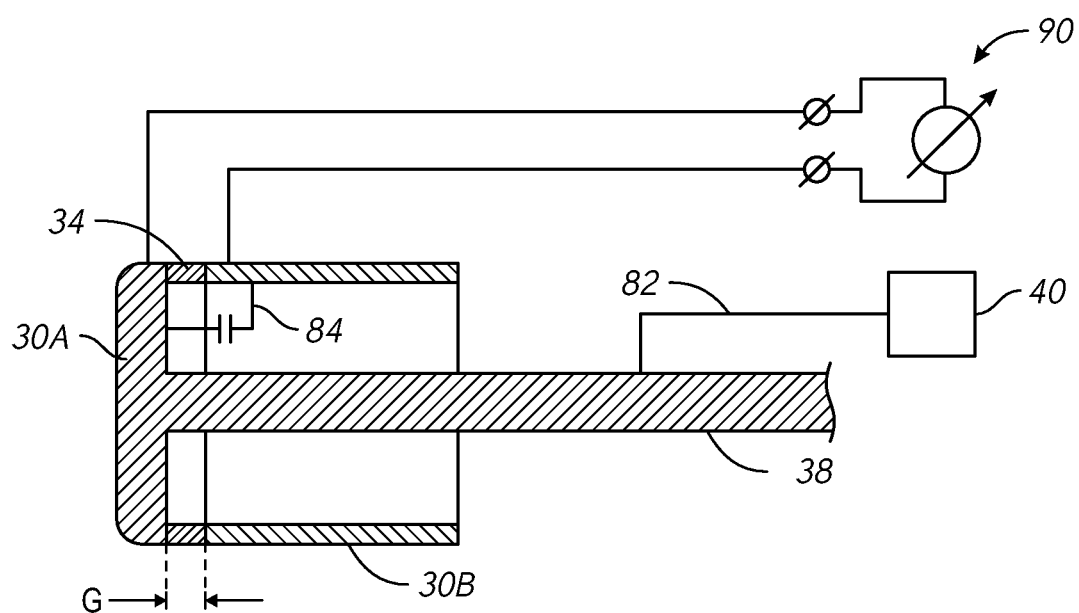
FIG. 6 schematically illustrates one embodiment of a high-pass filtering element consisting of a coupling capacitor. The filtering element can be incorporated into a system's catheter that comprises a high-resolution-tip design.

One embodiment of a configuration that can be used to balance the electrical current load delivered to each of the electrodes or electrode portions in a high-resolution tip design is schematically illustrated in FIG. 6. As shown, one of the electrodes (e.g., the distal electrode) 30A can be electrically coupled to an energy delivery module 40 (e.g., a RF generator). As discussed herein, the module 40 can comprise one or more components or features, such as, for example, an energy generation device that is configured to selectively energize and/or otherwise activate the energy members (e.g., RF electrodes), one or more input/output devices or components, a processor (e.g., a processing or control unit) that is configured to regulate one or more aspects of the treatment system, a memory and/or the like. Further, such a module can be configured to be operated manually or automatically, as desired or required.

In the embodiment that is schematically depicted in FIG. 6, the distal electrode 30A is energized using one or more conductors 82 (e.g., wires, cables, etc.). For example, in some arrangements, the exterior of the irrigation tube 38 comprises and/or is otherwise coated with one or more electrically conductive materials (e.g., copper, other metal, etc.). Thus, as shown in FIG. 6, the conductor 82 can be placed in contact with such a conductive surface or portion of the tube 38 to electrically couple the electrode or electrode portion 30A to an energy delivery module. However, one or more other devices and/or methods of placing the electrode or electrode portion 30A in electrical communication with an energy delivery module can be used. For example, one or more wires, cables and/or other conductors can directly or indirectly couple to the electrodes, without the use of the irrigation tube.

With continued reference to FIG. 6, the first or distal electrode or electrode portion 30A can be electrically coupled to the second or proximal electrode or electrode portion 30B using one more band-pass filtering elements 84, such as a capacitor, a filter circuit, etc. For instance, in some embodiments, the band-pass filtering element 84 comprises a capacitor that electrically couples the two electrodes or electrode portions 30A, 30B when radiofrequency current is applied to the system. In one embodiment, the capacitor 84 comprises a 100 nF capacitor that introduces a series impedance lower than about 3Ω at 500 kHz, which, according to some arrangements, is a target frequency for RF ablation. However, in other embodiments, the capacitance of the capacitor(s) or other band-pass filtering elements 84 that are incorporated into the system can be greater or less than 100 nF, for example, 5 nF to 300 nF, according to the operating RF frequency, as desired or required. In some embodiments, the capacitance of the filtering element 84 is selected based on a target impedance at a particular frequency or frequency range. For example, in some embodiments, the system can be operated at a frequency of 200 kHz to 10 MHz (e.g., 200-300, 300-400, 400-500, 500-600, 600-700, 700-800, 800-900, 900-1000 kHz, up to 10 MHz or higher frequencies between the foregoing ranges, etc.). Thus, the capacitor that couples adjacent electrodes or electrode portions to each other can be selected based on the target impedance for a particular frequency. For example, a 100 nF capacitor provides about 3Ω of coupling impedance at an operating ablation frequency of 500 kHz.

In some embodiments, a series impedance of 3Ω across the electrodes or electrode portions 30A, 30B is sufficiently low when compared to the impedance of the conductor 82

(e.g., wire, cable, etc.), which can be about 5-10Ω, and the impedance of tissue, which can be about 100Ω, such that the resulting tissue heating profile is not negatively impacted when the system is in use. Thus, in some embodiments, a filtering element is selected so that the series impedance across the electrodes or electrode portions is lower than the impedance of the conductor that supplies RF energy to the electrodes. For example, in some embodiments, the insertion impedance of the filtering element is 50% of the conductor 82 impedance, or lower, or 10% of the equivalent tissue impedance, or lower.

In some embodiments, a filtering element (e.g., capacitor a filter circuit such as the one described herein) can be located at a variety of locations of the device or accompanying system. For example, in some embodiments, the filtering element is located on or within a catheter (e.g., near the distal end of the catheter, adjacent the electrode, etc.). In other embodiments, however, the filtering element is separate of the catheter. For instance, the filtering element can be positioned within or along a handle to which the catheter is secured, within the generator or other energy delivery module, within a separate processor or other computing device or component and/or the like).

Figure 7:
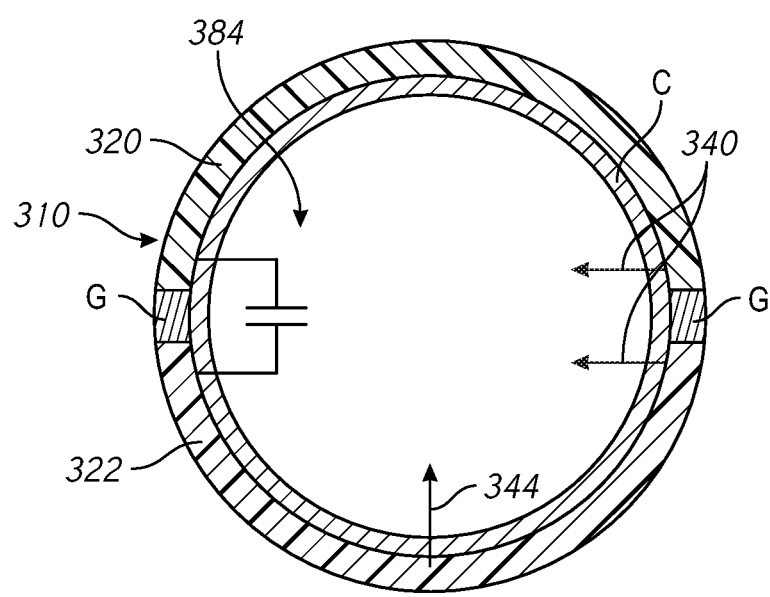
FIG. 7 schematically illustrates one embodiment of four high-pass filtering elements comprising coupling capacitors. The filtering elements can operatively couple, in the operating RF frequency range, the separate electrode sections of a system's catheter electrodes, e.g., those illustrated in FIG. 5.

Similarly, with reference to the schematic of FIG. 7, a filtering element 384 can be included in an electrode 310 comprising circumferentially-arranged portions 320, 322. In FIG. 7, the filtering element 384 permits the entire electrode 310 to be energized within RF frequency range (e.g., when the electrode is activated to ablate). One or more RF wires or other conductors 344 can be used to deliver power to the electrode from a generator or source. In addition, separate conductors 340 can be used to electrically couple the electrode 310 for mapping purposes.

In embodiments where the high-resolution-tip design (e.g., FIG. 4) comprises three or more electrodes or electrode portions, additional filtering elements (e.g., capacitors) can be used to electrically couple the electrodes or electrode portions to each other. Such capacitors or other filtering elements can be selected to create a generally uniform heating profile along the entire length of the high-resolution tip electrode. As noted in greater detail herein, for any of the embodiments disclosed herein or variations thereof, the filtering element can include something other than a capacitor. For example, in some arrangements, the filtering element comprises a LC circuit (e.g., a resonant circuit, a tank circuit, a tuned circuit, etc.). Such embodiments can be configured to permit simultaneous application of RF energy and measurement of EGM recordings.

As discussed above, the relatively small gap G between the adjacent electrodes or electrode portions 30A, 30B can be used to facilitate high-resolution mapping of the targeted tissue. For example, with continued reference to the schematic of FIG. 6, the separate electrodes or electrode portions 30A, 30B can be used to generate an electrogram that accurately reflects the localized electrical potential of the tissue being treated. Thus, a physician or other practitioner using the treatment system can more accurately detect the impact of the energy delivery to the targeted tissue before, during and/or after a procedure. For example, the more accurate electrogram data that result from such configurations can enable the physician to detect any gaps or portions of the targeted anatomical region that was not properly ablated or otherwise treated. Specifically, the use of a high-resolution tip design can enable a cardiac electrophysiologist to more accurately evaluate the morphology of resulting electrograms, their amplitude and width and/or to determine pacing thresholds. In some embodiments, morphology, amplitude and pacing threshold are accepted and reliable EP markers that provide useful information about the outcome of an ablation or other heat treatment procedure.

Figure 8:
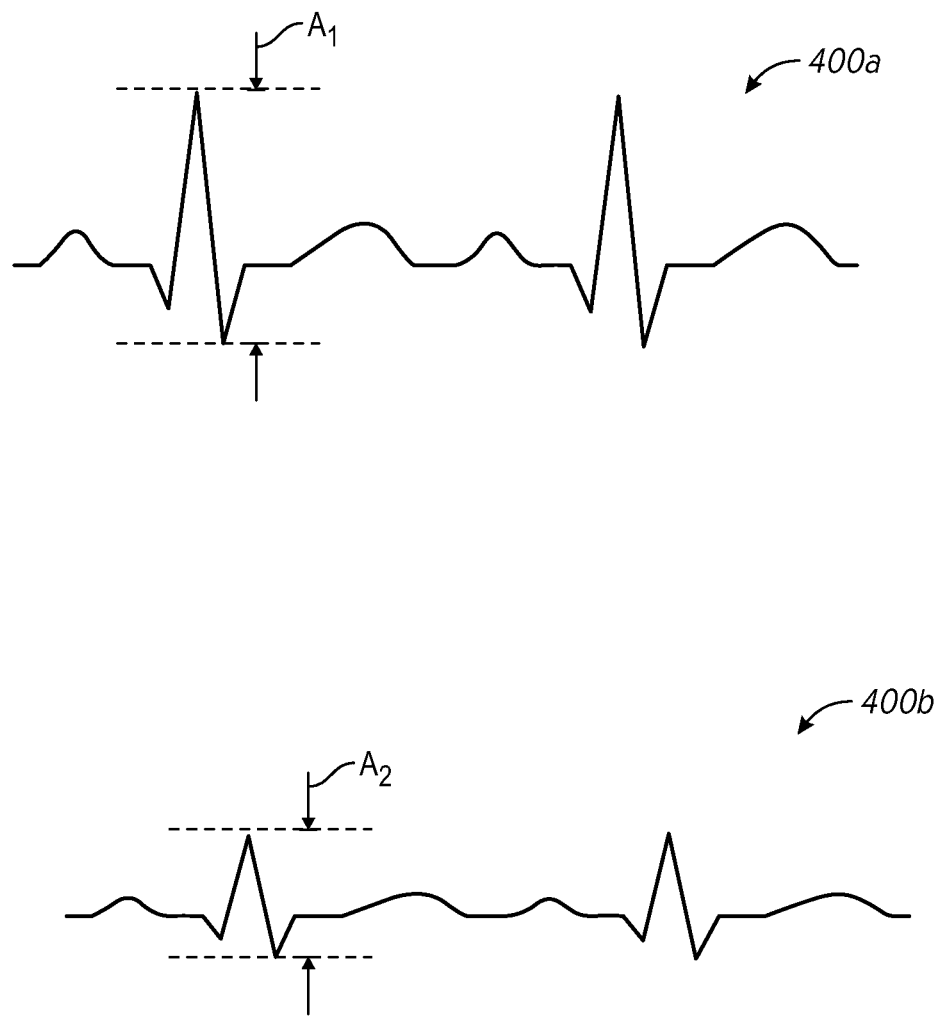
FIG. 8 illustrates embodiments of EKGs obtained from a high-resolution-tip electrode systems disclosed herein configured to detect whether an ablation procedure has been adequately performed.

According to some arrangements, the high-resolution-tip electrode embodiments disclosed herein are configured to provide localized high-resolution electrogram. For example, the electrogram that is obtained using a high-resolution-tip electrode, in accordance with embodiments disclosed herein, can provide electrogram data (e.g., graphical output) 400a, 400b as illustrated in FIG. 8. As depicted in FIG. 8, the localized electrograms 400a, 400b generated using the high-resolution-tip electrode embodiments disclosed herein include an amplitude A1, A2.

With continued reference to FIG. 8, the amplitude of the electrograms 400a, 400b obtained using high-resolution-tip electrode systems can be used to determine whether targeted tissue adjacent the high-resolution-tip electrode has been adequately ablated or otherwise treated. For example, according to some embodiments, the amplitude A1 of an electrogram 400a in untreated tissue (e.g., tissue that has not been ablated or otherwise heated) is greater that the amplitude A2 of an electrogram 400b that has already been ablated or otherwise treated. In some embodiments, therefore, the amplitude of the electrogram can be measured to determine whether tissue has been treated. For example, the electrogram amplitude A1 of untreated tissue in a subject can be recorded and used as a baseline. Future electrogram amplitude measurements can be obtained and compared against such a baseline amplitude in an effort to determine whether tissue has been ablated or otherwise treated to an adequate or desired degree.

In some embodiments, a comparison is made between such a baseline amplitude (A1) relative to an electrogram amplitude (A2) at a tissue location being tested or evaluated. A ratio of A1 to A2 can be used to provide a quantitative measure for assessing the likelihood that ablation has been completed. In some arrangements, if the ratio (i.e., A1/A2) is above a certain minimum threshold, then the user can be informed that the tissue where the A2 amplitude was obtained has been properly ablated. For example, in some embodiments, adequate ablation or treatment can be confirmed when the A1/A2 ratio is greater than 1.5 (e.g., 1.5-1.6, 1.6-1.7, 1.7-1.8, 1.8-1.9, 1.9-2.0, 2.0-2.5, 2.5-3.0, values between the foregoing, greater than 3, etc.). However, in other embodiments, confirmation of ablation can be obtained when the ratio of A1/A2 is less than 1.5 (e.g., 1-1.1, 1.1-1.2, 1.2-1.3, 1.3-1.4, 1.4-1.5, values between the foregoing, etc.).

According to some embodiments, an ablation system is configured to operatively couple to a pacemaker or related system that is configured to selectively pace or increase the heart rate of a subject. As discussed in greater detail herein, the use of such pacing can be used to confirm whether targeted tissue (e.g., cardiac tissue) has been properly ablated. Accordingly, such a system and related method can provide the user with information for assessing the success of a treatment procedure. For example, data provided by the system can be used to determine if the targeted tissue has been properly ablated. Thus, the various systems, devices and methods disclosed herein can be used to ensure that a desired or required level of treatment to targeted tissue has been accomplished. The confirmation and other feedback provided by the various systems, devices and methods disclosed herein can be used in addition to or in lieu of any other protocols for confirming successful treatment of targeted tissue.

According to some embodiments, an energy delivery module (e.g., a radiofrequency generator or other energy delivery generator) of an ablation system can be configured to be coupled to a pacemaker device or system. In some embodiments, such a pacemaker comprises a separate device or system that is separate and distinct of the energy delivery module and/or other components of the ablation system. However, in other configurations, the pacemaker device or system can be integrated within the energy delivery module and/or any other component of the system.

Regardless of whether the pacemaker device or system is integrated within or separate from the energy delivery module (e.g., radiofrequency generator) and/or any other component of an ablation system, such a pacemaker device or system can be configured to selectively pace cardiac tissue or increase a heart rate of a subject being treated. According to some embodiments, such pacing or an increase in heart rate is performed for purposes of confirming successful ablation of targeted tissue (e.g., atrial, ventricular and/or other cardiac tissue), as discussed in greater detail herein. However, the use of pacing can be performed for one or more other purposes as well, either in addition to or in lieu of confirmation of ablation, as desired or required.

In some embodiments, the heart of the subject is selectively paced (e.g., the heart rate of the subject is increased) to a desired level by delivering a pacing signal to the heart via one or more electrodes. For example, as illustrated schematically in FIG. 9, a system 2000 can comprise an energy delivery module (e.g., a radiofrequency generator or other generator) 2240 that is configured to couple to a catheter or other medical instrument 2220. As shown in the depicted arrangement and discussed in greater detail herein with reference to one or more embodiments, the catheter or other medical instrument 2220 can comprise one or more high-resolution electrodes or electrode portions 2222, 2224 located along the distal end of the catheter or other medical instrument 2220. In some embodiments, such high-resolution electrodes or electrode portions 2222, 2224 are electrically coupled to each other using one or more filtering elements (e.g., capacitors, other filtering elements, etc.) that permit the electrodes or electrode portions 2222, 2224 to selectively deliver ablative (e.g., radiofrequency) energy to targeted tissue of a subject while permitting the electrodes or electrode portions to obtain high-resolution mapping data of adjacent tissue (e.g., when ablative energy is not being provided to the electrodes or electrode portions), as discussed herein. For example, and without limitation, the filtering element positioned between the electrodes or electrode portions 2222, 2224 in FIG. 9 comprises a capacitor.

Figure 9:
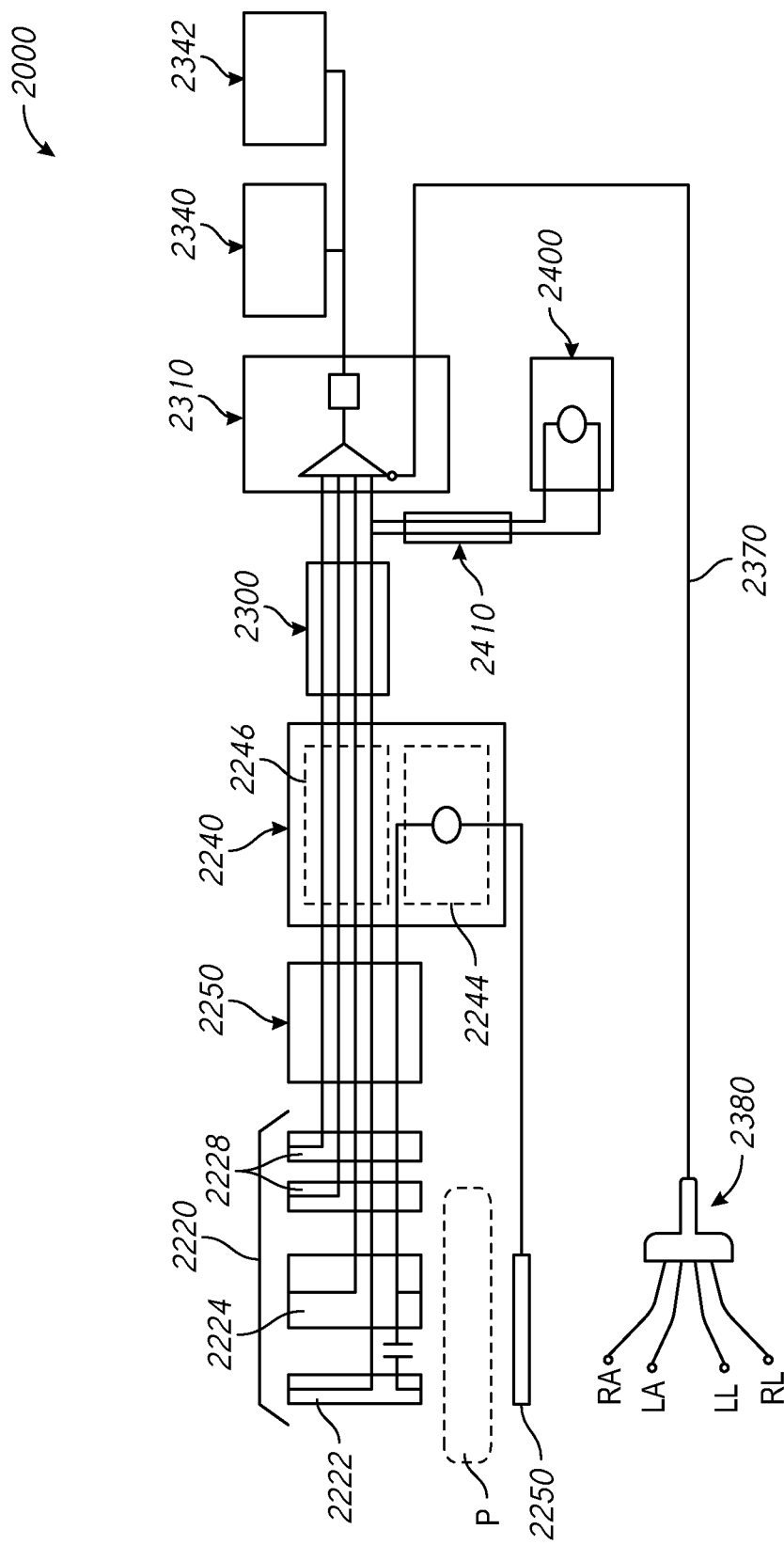
FIG. 9 schematically illustrates one embodiment of a mapping and ablation system configured for cardiac pacing.

With continued reference to FIG. 9, the system 2000 can further comprise a catheter cable 2250 that is used to physically and/or operatively couple the catheter or other medical instrument 2220 to the energy delivery module (e.g., RF generator) 2240. In some embodiments, such a cable or other connector 2250 can be physically incorporated into the design of the catheter or other medical instrument 2220. However, in other embodiments, the catheter cable 2250 can be separate and distinct from the catheter or other medical instrument 2220, as desired or required.

As shown in FIG. 9, the energy delivery module (e.g., a RF generator) can be configured to couple to a pacemaker device or system 2400. As noted herein, the pacemaker device or system can be incorporated into the energy delivery module 2240 or can be separate from it. Thus, in some embodiments, the RF generator or any other energy delivery module 2240 can include one or more ports and/or other couplings that are configured to receive, either directly or indirectly, a connection from a pacemaker device or system 2400 (e.g., an off-the-shelf or other third-party pacemaker device or system). In the embodiment schematically illustrated in FIG. 9, a pacemaker device or system 2400 is configured to indirectly couple to the energy delivery module 2240, as the pacemaker device or system 2400 connects or otherwise attaches or couples, via a pacemaker cable 2410, to a different component or device of the system 2000 (e.g., an EP recording system 2310, such as, a recording system provided by a third party, a recorder cable 2300 that operatively couples to the energy delivery module and/or EP recorder, etc.). However, in other arrangements, an energy delivery module (e.g., a RF generator) can be designed and otherwise configured to directly receive a pacemaker cable 2410 and/or other connection from a pacemaker device or system 2400, as desired or required. Any ports and/or other connection sites included in the RF generator (or other energy delivery module) 2240 and/or any other component of the system 2000 that is configured to receive a pacemaker cable 2410 or other connection from a pacemaker device or system 2400 can be standard or non-standard.

In some embodiments, once operatively coupled to an ablation/monitoring system 2000, a pacemaker device or system 2400 can be used to provide a pacing current to the catheter or other medical instrument 2220 in order to selectively increase the heart rate of the subject's heart. For example, in some embodiments, the heart rate of a subject can be increased from a baseline heart rate to 100-200 beats per minute, bpm, (e.g., 100-105, 105-110, 110-115, 115-120, 120-125, 125-130, 130-135, 135-140, 140-145, 145-150, 150-160, 160-170, 170-180, 180-190, 190-200 bpm, 120-150 bpm, frequencies between the foregoing, etc.) by delivering a pacing signal to the catheter.

Further, according to some embodiments, the pacing current generated by the pacemaker device or system 2400 is directed to and routed, at least partially, through the energy delivery module (e.g., RF generator) 2240. In some embodiments, the energy delivery module 2240 comprises a filter section 2246 through which the pacing current passes. According to some configurations, the filter section 2246 of the energy delivery module 2240 comprises low insertion impedance EGM filters that facilitate the delivery of the pacing current to the catheter or other medical instrument 2220 coupled to the energy delivery module 2240. Such filters can permit the system 2000 to deliver energy (e.g., radiofrequency energy, other ablative energy, etc.) to the electrode(s) of the catheter 2220 while simultaneously providing a desired pacing current to such electrode(s).

With continued reference to the schematic of FIG. 9, the energy delivery module (e.g., RF generator) 2240 can further include an energy delivery portion 2244. Accordingly, RF and/or other energy generated by the energy delivery module 2240 can be delivered to a catheter or other medical instrument 2220 to ablate or otherwise provide heat treatment to targeted tissue of a subject P. In some embodiments, the catheter or other medical instrument 2220 is coupled to the energy delivery module (e.g., RF generator) 2240 using a catheter cable 2250.

As discussed with reference to other embodiments herein, the catheter or other medical instrument 2220 that operatively couples to the energy delivery module 2240 can include a high-resolution electrode design. For example, in some embodiments, the catheter comprises an electrode that is configured to obtain high-resolution mapping data (e.g., when ablative energy is not being delivered to the electrode), in accordance with the various embodiments disclosed herein, or variations thereof. For example, a filtering element or other feature can advantageously permit the electrode along the distal end of the catheter or other medical instrument 2220 to obtain high resolution mapping data before and/or after ablative energy (e.g., radiofrequency energy) has been delivered to the catheter or other medical instrument 2220. In some embodiments, the design of such a high-resolution electrode assembly can permit a user to obtain and use accurate mapping data associated with the specific location of the electrode.

As schematically illustrated in FIG. 9, the catheter or other medical instrument 2220 of the system 2000 can comprise a high-resolution electrode assembly (e.g., first and second electrodes or electrode portions 2222, 2224 located along the distal end of the catheter or medical instrument). Further, in some embodiments, the catheter or other medical instrument 2220 can comprise one or more (e.g., 2, 3, more than 3, etc.) additional mapping electrodes (e.g., standard ring electrodes) located along or near the high-resolution electrodes or electrode portions. For example, in some embodiments, a catheter 2220 can include two ring electrodes 2228 that are located proximal to the high-resolution electrode(s) or electrode portion(s) and that are configured to obtain mapping data from surrounding tissue of the subject.

In some embodiments, any of the cardiac pacing concepts disclosed herein (e.g., the ability to provide pacing currents to a catheter or other medical instrument, the ability to pace or increase the heart rate of a subject prior to or during a cardiac treatment procedure, etc.) can be used with catheters or other medical instruments that do not include high-resolution mapping electrodes or related features. Thus, the pacing concepts (e.g., and the related confirmation of ablation of targeted tissue) can be incorporated into any energy delivery and/or mapping technologies, regardless of whether they are specifically described or otherwise disclosed herein.

According to some embodiments, pacing currents can be provided to the electrode or other energy delivery device of a catheter (or other medical instrument). In some arrangements, the pacing current that is provided to the electrode or other energy delivery device is greater than the pre-ablation pacing threshold level, but lower than the post-ablation pacing threshold level. For example, once paced (e.g., using the current or signal provided by the pacemaker device or system 2400), the subject's heart will be paced (e.g., the subject's heart rate will increase to an elevated heart rate frequency or level). As discussed in greater detail herein, for instance, the pacemaker signal can increase the subject's heart rate to 100-150 beats per minute (bpm), e.g., 100-105, 105-110, 110-115, 115-120, 120-125, 125-130, 130-135, 135-140, 140-145, 145-150 bpm, value between the foregoing ranges, etc.). In other embodiments, the pacing can increase a subject's heart rate to levels exceeding 150 bpm (e.g., 150-160, 160-170, 170-180 bpm, values between the foregoing ranges, values greater than 180 bpm, etc.) or less than 100 bpm (e.g., 70-75, 75-80,80-85, 85-90, 90-95, 95-100 bpm, values between the foregoing ranges, values less than 70 bpm, etc.), as desired to required.

According to some embodiments, as indicated above, the pacing current provided by the pacemaker device or system 2400 coupled to (or integrated with) the energy delivery module (e.g., the RF generator) 2240 will exceed a pre-ablation pacing threshold. In other words, the pacing current will be configured to stimulate the subject's heart to a desired elevated rate or level and will also be configured to surpass the pacing threshold at which the targeted tissue of the subject will be ablated or otherwise heat-treated to a desired level.

In some embodiments, the pacing current provided by the pacemaker device or system 2400 is greater than 15 milliamps (mA). For example, the pacing current provided by the pacemaker device or system is 15-20 milliamps (mA), e.g., 15-16, 16-17, 17-18, 18-19, 19-20 mA, currents between the foregoing ranges, etc. In other embodiments, the pacing current provided by the pacemaker device or system is less than 15 mA (e.g., 10-11, 11-12, 12-13, 13-14, 14-15 mA, currents between the foregoing ranges, etc.) or greater than 20 mA, (e.g., 20-21, 21-22, 22-23, 23-24, 24-25, 25-30 mA, currents between the foregoing ranges, currents greater than 30 mA, etc.), as desired or required. In some embodiments, the pacing current provided by the pacemaker device or system is 5 to 20 mA (e.g., 10-15 mA).

Regardless of the exact pacing current provided to the electrode(s) or electrode portion(s) of the catheter or other medical instrument by the pacemaker device or system, the heart rate of the subject being treated will increase above the subject's baseline (e.g., normal) heart rate. In some embodiments, the formation of a lesion or the completion of heat treatment of the targeted tissue will cause the pacing threshold to increase considerably, from pre-ablation levels (e.g. 1 to 5 mA) to post-ablation levels (e.g. 15 to 20 mA, or greater). By way of example, and without limitation, in some embodiments, it is possible that the pre-ablation pacing threshold is approximately 1 mA and the post-ablation pacing threshold is approximately 20 mA. In such circumstances, application of pacing currents of 10 mA would produce "heart capture," meaning an increase of the heart rate to the rate programmed on pacemaker device or system 2400. With successful ablation treatment, as the pacing threshold increases, the user will observe the cessation of pacing signals being propagated through such a lesion or treated tissue, as the post-ablation pacing threshold exceeds the pacing current amplitude (e.g., in the specific, non-limiting example provided above, 20 mA is greater than 10 mA). As a result, the heart rate of the subject being treated will drop to a level below the elevated heart rate induced by the pacing signal generated by the pacemaker device or system. The loss of such an elevated pacing rate of cardiac tissue is referred to as "loss of capture," providing another form of confirmation to a user that the targeted tissue has been properly treated (e.g., ablated).

In some embodiments, such confirmation of adequate ablation of tissue can help prevent overheating of targeted tissue, as the user is notified in a prompt manner that loss of capture (e.g., or a desired level of tissue ablation) has been attained. As a result, the likelihood of charring or overheating of targeted tissue can be prevented. This can help ensure that undesirable damage to the targeted tissue is avoided and/or that damage to tissue surrounding or adjacent to the targeted tissue is not inadvertently harmed.

The use of high-resolution electrode(s) or electrode portion(s) further enhances the pacing data obtained by the system, in accordance with several embodiments. For example, in some embodiments, the ability of high-resolution electrode(s) or electrode portion(s), in accordance with the various configurations described herein or variations thereof to pace the cardiac tissue located in its immediate vicinity ensures that the devices, systems, methods and techniques disclosed herein have high specificity. As a result, pacing of far-field tissues is avoided. Therefore, the technique advantageously monitors the localized effects of cardiac ablation. As a result, the cardiac data obtained using the system are specific to the anatomical region adjacent the high-resolution electrode, providing a more accurate representation of the condition of the targeted tissue. Thus, the likelihood of overheating targeted tissue is advantageously reduced.

According to some embodiments, the pre-ablation pacing threshold is greater than 1 or 2 milliamps (mA). For example, the pre-ablation pacing threshold is 1-5 mA (e.g., 1-1.5, 1.5-2, 2-2.5, 2.5-3, 3-3.5, 3.5-4, 4-4.5, 4.5-5 mA, values between the foregoing ranges, etc.). However, in other embodiments, the pre-ablation pacing threshold is greater than 5 mA (e.g., 5-6, 6-7, 7-8 mA, values between the foregoing ranges, greater than 8 mA, etc.) or less than 1 mA (e.g., 0.1-0.2, 0.2-0.3, 0.3-0.4, 0.4-0.5, 0.5-0.6, 0.6-0.7, 0.7-0.8, 0.8-0.9, 0.9-1 mA, values between the foregoing ranges, values less than 0.1 mA, etc.), as desired or required. In some embodiments, the pre-ablation pacing threshold is 0.1 to 5 mA (e.g., 0.5-2 mA). In addition, in some configurations, the post-ablation pacing threshold is greater than 10 milliamps (mA). For example, the post-ablation pacing threshold is 10-15 mA (e.g., 10-11, 11-12, 12-13, 13-14, 14-15 mA, values between the foregoing ranges, values greater than 15 mA, etc.). However, in other embodiments, the post-ablation pacing threshold is less than 10 mA (e.g., 5-6, 6-7, 7-8, 8-9, 9-10 mA, values between the foregoing ranges, less than 5 mA, etc.), as desired or required. Conversely, in other embodiments, the post-ablation pacing threshold may exceed 20 mA. In some embodiments, the post-ablation pacing threshold exceeds 10 mA or 20 mA.

According to some arrangements, once loss of capture is achieved (e.g., confirmation of ablation or desired/required heat treatment of targeted tissue is received by and/or communicated to a user), the system 2000 can be configured to terminate the delivery of RF (or other energy) from the energy delivery module 2240 (e.g., RF generator) to the catheter or other medical instrument 2220, either immediately or following a particular time period. In some embodiments, a processor or other control unit of the energy delivery module (and/or any other processor or control unit external to the energy delivery module or system) can be configured to automatically terminate (or alter, e.g., modulate or slow down) the delivery of RF or other energy to the catheter or other medical instrument once loss of capture has been attained.

In other embodiments, however, a processor or other portion of the system (and/or operatively coupled to the system) can be configured to automatically terminate (or alter) a delivery of energy (e.g., RF) to the catheter or other medical instrument after a certain time period after loss of capture has been attained. For example, according to some arrangements, the processor or other control unit of the energy delivery module (e.g., RF generator) and/or any other processor or control unit operatively coupled to the system 2000 can be configured to permit the delivery of energy to the electrode(s) or other energy delivery member of the catheter or other medical instrument for 0.5-5 seconds (e.g., 0.5-1, 1-1.5, 1.5-2, 2-2.5, 2.5-3, 3-3.5, 3.5-4, 4-4.5, 4.5-5 seconds, time periods between the foregoing ranges, etc.) after loss of capture has been achieved. In other embodiments, the delivery of energy can continue for a time period greater than 5 seconds after loss of capture (e.g., 5-6, 6-7, 7-8, 8-9, 9-10, 10-15, 15-20, 20-30 seconds, time periods between the foregoing ranges, greater than 30 seconds, etc.). In some embodiments, such a protocol or configuration can help ensure that proper ablation has been accomplished.

According to some embodiments, the confirmation of completed ablation using the pacing of cardiac tissue and the subsequent loss of capture can be used either in lieu of or in addition to other metrics, techniques, tools and/or methods, such as, for example, ECG amplitude reductions, visual evidence of lesion formation (e.g., fluoro and/or ultrasound imaging, other imaging, etc.) and/or the like, regardless of whether such confirmation tools are specifically disclosed herein. For example, in some embodiments, the confirmation procedures relating to pacing and loss of capture are used as the sole or primary method of confirming proper ablation of targeted tissue. However, in other configurations, the use of such techniques and methods can be used to confirm or otherwise validate results and data obtained using one or more other techniques or methods, as desired or required.

With continued reference to the schematic of FIG. 9, the system 2000 can additionally include (or be operatively coupled with) an EP recording system 2310 through which various mapping and other signals (e.g., ECG signals) are received and/or processed. In some embodiments, one or more output devices 2340, 2342 (e.g., displays, other screens, etc.) can be provided to visually display data and/or other information relevant to a procedure being conducted by the system 2000. For example, in some embodiments, the displays and/or other output devices 2340, 2342 can be configured to receive pacing or heart rate data obtained using the high-resolution electrode(s) or electrode portion(s), ECG data (e.g., obtained from high-resolution electrodes or electrode portions), tissue contact data, imaging data and graphical representations and/or the like. Further, in order to obtain, collect and/or process the necessary data, the system 2000 can include one or more of the following: a return electrode 2250 (e.g. positioned along the lower portion of a subject P), an ECG cable that operatively couples the system 2000 to surface and/or other ECG electrodes (e.g., to provide ECG data before, during and/or after a procedure) and/or the like.

Figure 10:
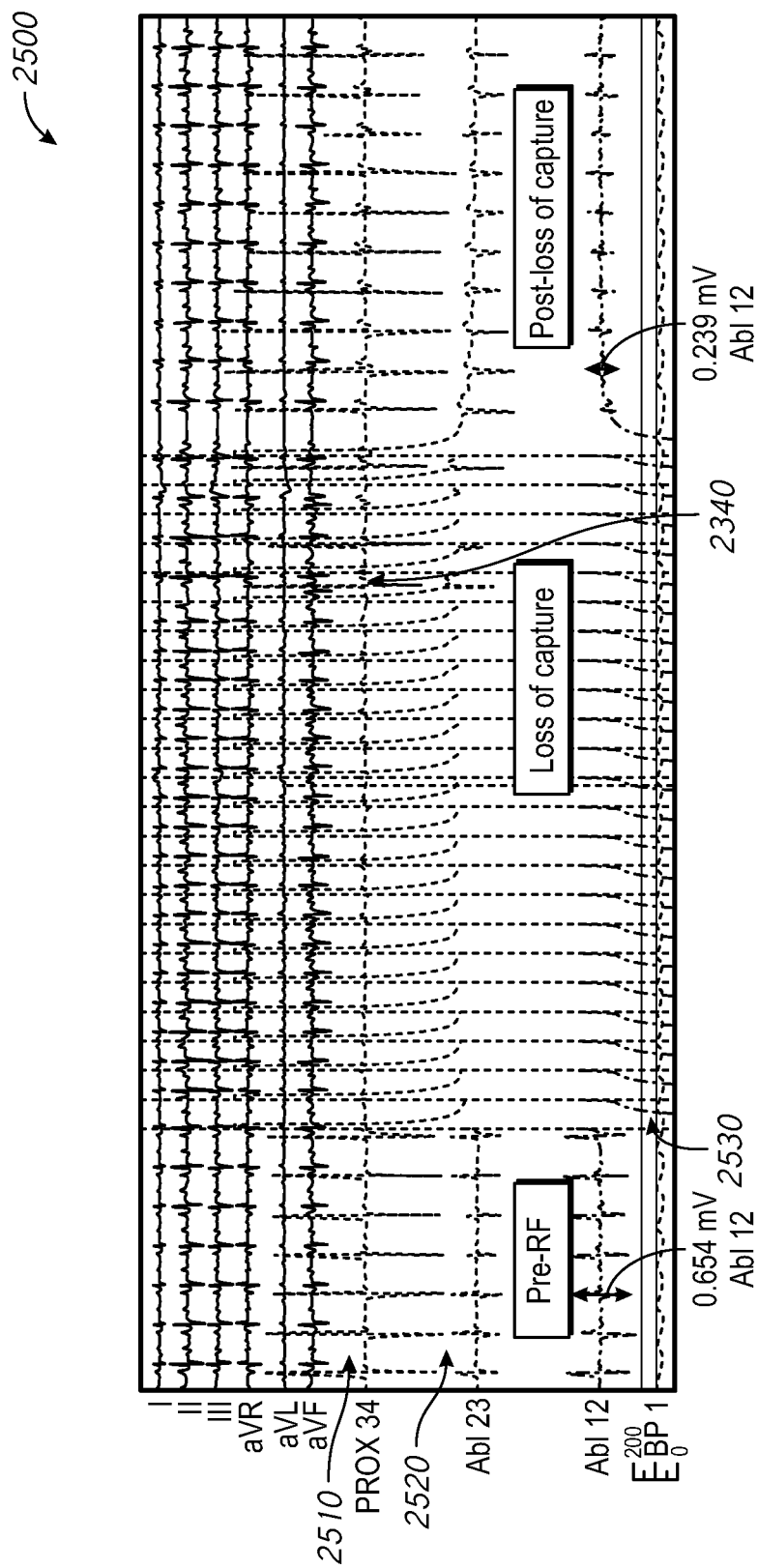
FIG. 10 illustrates one embodiment of a graphical output using a mapping and ablation system, such as the system schematically depicted in FIG. 9.

FIG. 10 illustrates one embodiment of a graphical data output 2500 (e.g., as provided by the system to a display or other output device). As shown, the graphical output 2500 comprises various charts indicative of one or more data sets obtained by an ablation system before, during and after the execution of an ablation procedure. For example, in the illustrated embodiment, graphs 2510 are provided regarding ECG data that are obtained by the electrodes of the catheter. Further, the output 2500 comprises a graphical representation 2530 of the heart rate. In some embodiments, as discussed herein, a pacing signal can be provided to the system (e.g., via a pacemaker device or system that is operatively coupled to the RF generator or other energy delivery module) to increase the heart rate of the subject being treated. This is visible in the embodiment of FIG. 10 when the graphical representation 2530 of the heart rate of the subject increases (e.g., the rate of cardiac activity of the subject increases). Once sufficient RF and/or other energy has been delivered to the targeted tissue adjacent the high-resolution electrode, in accordance with the foregoing disclosure, the post-ablation pacing threshold will exceed the amplitude of the pacing current, as a confirmation that ablating the targeted tissue was successful in rendering such tissue non-viable. Accordingly, the measured heart rate will drop, providing graphical confirmation 2340 of loss of capture to a user. As noted herein, once loss of capture has been confirmed, the user manually (and/or the system, e.g., automatically) can terminate an ablation procedure, either immediately or following a desired period, in accordance with a particular protocol or treatment technique.

According to some embodiments, due to the nature of the high-resolution-tip electrode systems that are used to create a more complete and comprehensive map of targeted tissue, in accordance with the various high-resolution-tip systems and devices disclosed herein, additional information regarding the position of the roving catheter (and thus, the intermediate mapping locations) can be obtained and provided to the user during a procedure. For example, given the high-resolution mapping capabilities of such catheters, information can be obtained regarding the nature, type and other details regarding the tissue that is adjacent the electrode. In addition, as noted above, the high-resolution-tip embodiments disclosed herein can help determine whether a specific tissue region has been adequately ablated (e.g., see the disclosure above with reference to FIG. 8).

In some embodiments, any of the high-resolution-tip electrode devices or systems disclosed herein can be used as stand-alone mapping systems to accurately assess the condition of a subject's targeted anatomical region, even with the use of a separate mapping system. For example, a user can move a high-resolution-tip electrode catheter or other medical instrument to various locations within a subject's anatomy to generate a detailed, accurate and complete electrical map, as desired or required.

As a result of the high-resolution mapping capabilities of the various high-resolution-tip electrode catheter devices and systems disclosed herein, an accurate map of the subject's targeted anatomical space or other region can be obtained. In addition, in view of the fact that such systems are also configured to advantageously ablate tissue, a more efficient and accurate treatment procedure can be attained. For example, in embodiments where one of the high-resolution-tip electrodes devices or systems disclosed herein is being use to map a subject's anatomy (e.g., atrium), either with or without the use of a separate (e.g., commercially-available mapping system), such a high-resolution-tip device or system can be used to also ablate tissue. This can facilitate and improve the execution of a treatment procedure. For example, the ability to use a single device to both map and ablate tissue permits a user to more expeditiously perform an overall assessment and treatment of a subject. In addition, the ability to create a more comprehensive map of the subject's tissue, allows a user to perform a subject treatment procedure with greater accuracy and precision. As discussed, this can help reduce the overall (and sometimes unnecessary) trauma to the subject, improve recovery and provide for better and effective treatment of the subject's disease. In addition, as noted above, the ability of the user to determine whether tissue has already been ablated or otherwise treated to a sufficient level can further improve the efficacy, efficiency and/or safety of a procedure.

In some embodiments, the system comprises various features that are present as single features (as opposed to multiple features). For example, in one embodiment, the system includes a single catheter that is configured to obtain high-resolution mapping of tissue. The system can include a single energy delivery module (e.g., a generator) for supplying ablative or other energy to the catheter. The system can further include a single processor that is configured to regulate the delivery of energy from the energy delivery module to the catheter. The catheter can include a split-tip electrode design and/or any other high-resolution configuration. The system can include a single pacemaker (e.g., that is integrated with or separate from the energy delivery module and/or any other component of the system) to selectively pace or increase the heartrate of a subject's heart.

According to some embodiments, the system consists essentially of a catheter that is configured to obtain high-resolution mapping of tissue, an energy delivery module (e.g., a RF or other generator) for supplying ablative or other energy to the catheter, and a processor that is configured to regulate the delivery of energy from the energy delivery module to the catheter. According to some embodiments, the system consists essentially of a catheter that is configured to obtain high-resolution mapping of tissue, an energy delivery module (e.g., a RF or other generator) for supplying ablative or other energy to the catheter, a processor that is configured to regulate the delivery of energy from the energy delivery module to the catheter and a pacemaker for selectively pacing the heart of the subject being treated.

In some embodiments, the system comprises one or more of the following: means for tissue modulation (e.g., an ablation or other type of modulation catheter or delivery device), means for generating energy (e.g., a generator or other energy delivery module), means for connecting the means for generating energy to the means for tissue modulation (e.g., an interface or input/output connector or other coupling member), means for increasing the heartrate of a subject being treated (e.g., using a pacemaker that is integrated with or separate from one or more components of the system), etc.

Any methods described herein may be embodied in, and partially or fully automated via, software code modules executed by one or more processors or other computing devices. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

In addition, embodiments may be implemented as computer-executable instructions stored in one or more tangible computer storage media. As will be appreciated by a person of ordinary skill in the art, such computer-executable instructions stored in tangible computer storage media define specific functions to be performed by computer hardware such as computer processors. In general, in such an implementation, the computer-executable instructions are loaded into memory accessible by at least one computer processor. The at least one computer processor then executes the instructions, causing computer hardware to perform the specific functions defined by the computer-executable instructions. As will be appreciated by a person of ordinary skill in the art, computer execution of computer-executable instructions is equivalent to the performance of the same functions by electronic hardware that includes hardware circuits that are hardwired to perform the specific functions. As such, while embodiments illustrated herein are typically implemented as some combination of computer hardware and computer-executable instructions, the embodiments illustrated herein could also be implemented as one or more electronic circuits hardwired to perform the specific functions illustrated herein.

The various systems, devices and/or related methods disclosed herein can be used to at least partially ablate and/or otherwise ablate, heat or otherwise thermally treat one or more portions of a subject's anatomy, including without limitation, cardiac tissue (e.g., myocardium, atrial tissue, ventricular tissue, valves, etc.), a bodily lumen (e.g., vein, artery, airway, esophagus or other digestive tract lumen, urethra and/or other urinary tract vessels or lumens, other lumens, etc.), sphincters, other organs, tumors and/or other growths, nerve tissue and/or any other portion of the anatomy. The selective ablation and/or other heating of such anatomical locations can be used to treat one or more diseases or conditions, including, for example, atrial fibrillation, mitral valve regurgitation, other cardiac diseases, asthma, chronic obstructive pulmonary disease (COPD), other pulmonary or respiratory diseases, including benign or cancerous lung nodules, hypertension, heart failure, denervation, renal failure, obesity, diabetes, gastroesophageal reflux disease (GERD), other gastroenterological disorders, other nerve-related disease, tumors or other growths, pain and/or any other disease, condition or ailment.

In any of the embodiments disclosed herein, one or more components, including a processor, computer-readable medium or other memory, controllers (for example, dials, switches, knobs, etc.), displays (for example, temperature displays, timers, etc.) and/or the like are incorporated into and/or coupled with (for example, reversibly or irreversibly) one or more modules of the generator, the irrigation system (for example, irrigant pump, reservoir, etc.) and/or any other portion of an ablation or other modulation system.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter" or "delivering energy to an ablation member" include "instructing advancing a catheter" or "instructing delivering energy to an ablation member," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. An energy delivery module configured to deliver ablative energy to targeted cardiac tissue of a subject and for confirming successful ablation of said targeted cardiac tissue, comprising:
    a processor for regulating the delivery of ablative energy;
    wherein the energy delivery module is configured to operatively couple to a catheter, wherein the energy delivery module is configured to energize a high-resolution electrode positioned along a distal end of the catheter to selectively ablate said targeted cardiac tissue adjacent the high-resolution electrode;
    wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level; and
    wherein the processor is configured to terminate the delivery of ablative energy to the high-resolution electrode after loss of capture of the heart of the subject,
    wherein the high-resolution electrode comprises a distal portion and a proximal portion, wherein the distal and proximal portions function as a single electrode when the ablative energy is delivered by the high-resolution electrode to the targeted cardiac tissue; and wherein the distal and proximal portions of the high-resolution electrode are operatively coupled to each other using at least one filtering element.

2. The energy delivery module of claim 1, further comprising the pacemaker, wherein the pacemaker is integrated within the energy delivery module.

3. The energy delivery module of claim 1, further comprising the pacemaker.

4. The energy delivery module of claim 1, wherein the pacemaker is integrated within the energy delivery module.

5. The energy delivery module of claim 1, wherein the pacemaker is separate from the energy delivery module.

6. A kit for delivering ablative energy to targeted cardiac tissue of a subject and for confirming successful ablation of said targeted cardiac tissue, comprising:
    a catheter comprising a high-resolution electrode along a distal end of the catheter; and
    an energy delivery module comprising a processor, wherein the processor is configured to regulate the delivery of ablative energy;
    wherein the energy delivery module is configured to operatively couple to the catheter, wherein the energy delivery module is configured to energize the high-resolution electrode positioned along a distal end of the catheter to selectively ablate said targeted cardiac tissue adjacent the high-resolution electrode;
    wherein the processor is configured, via a predetermined pacing signal provided to the catheter by a pacemaker, to increase the heart rate of the subject from a baseline level to an elevated level, the predetermined pacing signal comprising a pacing level greater than a pre-ablation pacing threshold level; and
    wherein the processor is configured to terminate the delivery of ablative energy to the high-resolution electrode after loss of capture of the heart of the subject,
    wherein the high-resolution electrode comprises a distal portion and a proximal portion, wherein the distal and proximal portions function as a single electrode when the ablative energy is delivered by the high-resolution electrode to the targeted cardiac tissue; and wherein the distal and proximal portions of the high-resolution electrode are operatively coupled to each other using at least one filtering element.

7. The kit of claim 6, further comprising the pacemaker, wherein the pacemaker is separate from the energy delivery module.

8. The kit of claim 6, further comprising the pacemaker.

9. The kit of claim 6, wherein the pacemaker is integrated within the energy delivery module.

10. The kit of claim 6, wherein the pacemaker is separate from the energy delivery module.

11. A generator configured to deliver ablative energy to targeted cardiac tissue of a subject and for confirming successful ablation of said targeted cardiac tissue, comprising:
- an energy delivery module configured to generate ablative energy for delivery to an ablation device; and
- a processor configured to regulate the delivery of ablative energy from the energy delivery module to a high-resolution electrode of the ablation device;
- wherein ablative energy generated by the energy delivery module is delivered to the high-resolution electrode;
- wherein the processor is configured, via a predetermined pacing signal provided to the high-resolution electrode by a pacemaker, to increase the heart rate of the subject from a baseline level to an elevated level, the predetermined pacing signal comprising a pacing level greater than a pre-ablation pacing threshold level; and
- wherein the processor is configured to terminate the delivery of energy to the high-resolution electrode after loss of capture of the heart of the subject,
- wherein the high-resolution electrode comprises a distal portion and a proximal portion, wherein the distal and proximal portions function as a single electrode when the ablative energy is delivered by the high-resolution electrode to the targeted cardiac tissue; and wherein the distal and proximal portions of the high-resolution electrode are operatively coupled to each other using at least one filtering element.

12. The generator of claim 11, wherein the energy delivery module is configured to generate radiofrequency (RF) energy.

13. The generator of claim 11, wherein the processor and the energy delivery module are located within a single housing or enclosure.

14. The generator of claim 11, wherein the processor and the energy delivery module are located within separate housings or enclosures.

15. The generator of claim 11, further comprising the pacemaker.

16. The generator of claim 15, wherein the pacemaker is integral to the energy delivery module.

17. The generator of claim 15, wherein the pacemaker is separate from the energy delivery module.

18. The generator of claim 11, wherein the at least one filtering element comprises a capacitor.

* * * * *